United States Patent [19]

Takeuchi et al.

[11] Patent Number: 5,147,445
[45] Date of Patent: Sep. 15, 1992

[54] HERBICIDAL TRIAZOLE COMPOUNDS AND HERBICIDAL COMPOSITIONS CONTAINING THE SAME

[75] Inventors: Masaki Takeuchi, Saitama; Mitsuhiro Yasuda, Tokyo; Mitsuru Kanzaki, Shizuoka, all of Japan

[73] Assignee: Chugai Seiyaku Kabushiki Kaisha, Tokyo, Japan

[21] Appl. No.: 646,481

[22] Filed: Jan. 25, 1991

Related U.S. Application Data

[63] Continuation of Ser. No. 319,242, Jun. 6, 1989, abandoned.

[30] Foreign Application Priority Data

Mar. 7, 1988 [JP] Japan ............... 63-53153
Jul. 5, 1988 [JP] Japan ............... 63-16712
Aug. 31, 1988 [JP] Japan ............... 63-217722

[51] Int. Cl.$^5$ ................ A01N 43/653; C07D 249/12
[52] U.S. Cl. ................ 71/92; 548/264.2; 548/264.4
[58] Field of Search ............... 71/92; 548/264.2, 264.4

[56] References Cited

U.S. PATENT DOCUMENTS

| | | | |
|---|---|---|---|
| 3,308,131 | 3/1967 | McKusick | 548/263 |
| 3,816,392 | 6/1974 | Weaver et al. | 548/263 |
| 3,897,440 | 7/1975 | Beck et al. | 71/92 |
| 3,952,001 | 4/1976 | Brookes | 71/92 |
| 4,005,202 | 1/1977 | Beard et al. | 514/393 |
| 4,280,831 | 7/1981 | Patel | 71/92 |

FOREIGN PATENT DOCUMENTS

| | | | |
|---|---|---|---|
| 0140194 | 8/1985 | European Pat. Off. | |
| 59-39880 | 3/1984 | Japan | 548/265 |

*Primary Examiner*—Patricia L. Morris
*Attorney, Agent, or Firm*—Browdy and Neimark

[57] ABSTRACT

Novel triazole compounds represented by the general formulas I and II, a process for producing novel triazole compounds of the general formula I from novel triazole compounds of the general formula II as starting materials, and herbicides that include novel triazole compounds of the general formula I:

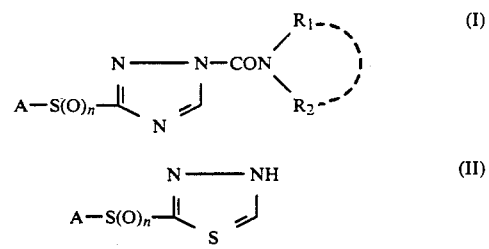

where
$R_1$ and $R_2$ which may be the same or different each represents a lower alkyl, cycloalkyl, alkenyl or alkynyl group, or $R_1$ and $R_2$, when taken together with the nitrogen atom to which they are bonded, represent an azacycloalkane having 4–6 carbon atoms;
A represents a group represented by one of the following formulas:

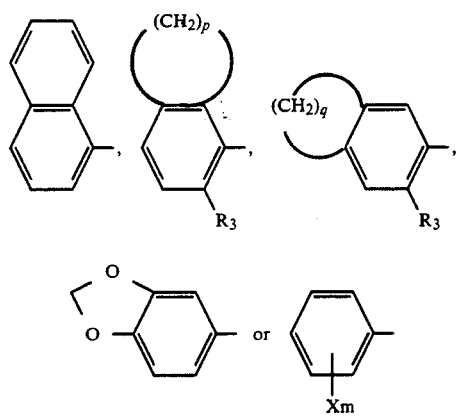

(where X is a hydrogen atom or an optionally hydroxyl substituted lower alkyl, cycloalkyl, alkoxy, alkoxycarbonyl, alkylcarbonyl, phenoxy, benzyl or α-hydroxybenzyl group, a halogen, a nitro group, an amino group or trifluoromethyl group; $R_3$ is a hydrogen atom or lower alkoxy; m is 0, 1, 2, 3 or 4; n is 0, 1 or 2; and p and q are each 2, 3, 4 or 5).

10 Claims, No Drawings

HERBICIDAL TRIAZOLE COMPOUNDS AND HERBICIDAL COMPOSITIONS CONTAINING THE SAME

This application is a continuation of parent, co-pending application Ser. No. 07/319,242, filed Mar. 6, 1989, now abandoned in favor of the present application.

BACKGROUND OF THE INVENTION

The present invention relates to novel triazole compounds represented by the general formula I:

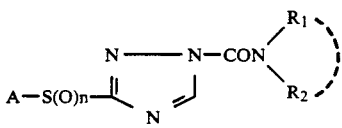

where
$R_1$ and $R_2$ which may be the same or different each represents a lower alkyl, cycloalkyl, alkenyl or alkynyl group, or $R_1$ and $R_2$, when taken together with the nitrogen atom to which they are bonded, represent an azacycloalkane having 4–6 carbon atoms;
A represents a group represented by one of the following formulas:

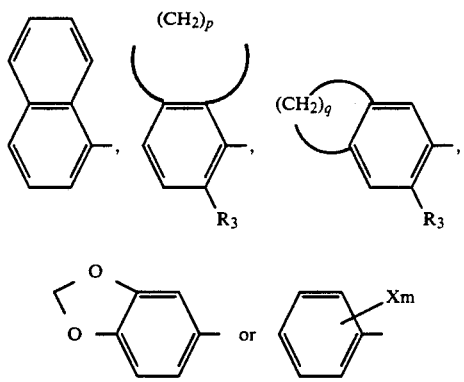

(where X is a hydrogen atom or an optionally hydroxyl substituted lower alkyl, cycloalkyl, alkoxy, alkoxycarbonyl, alkylcarbonyl, phenoxy, benzyl or α-hydroxybenzyl group, a halogen, a nitro group, an amino group or a trifluoromethyl group; $R_3$ is a hydrogen atom or lower alkoxy, preferably methoxy; m is 0, 1, 2, 3 or 4; n is 0, 1 or 2; and p and q are each 2, 3, 4 or 5). The present invention also relates to herbicides that contain these novel triazole compounds in admixture with one or more compounds selected from the group consisting of pyrazolate, pyrazoxyfen, benzofenap, bensulfuron methyl, pyrazosulfuron ethyl, bromobutide, clomeprop and CG-148 (the group of these compounds is hereinafter referred to as the group of known herbicides). The present invention also relates to a process for producing novel triazole compounds represented by the general formula I, as well as novel triazole compounds useful as starting materials in this process.

Some triazole compounds have bactericidal activities as taught in German Patent No. 2,132,618, U.S. Pat. No. 4,280,831, Japanese Patent Public Disclosure Nos. 59-39880, 60-100561, etc.

However, the conventional triazole herbicides harm crops or are unable to exhibit satisfactory herbicidal effects unless used in large amounts. A need has, therefore, existed for the development of triazole compounds that are free from these problems.

SUMMARY OF THE INVENTION

An object, therefore, of the present invention is to provide triazole compounds that cause little harm to crops and which need only be used in a low dose to exhibit marked herbicidal effects, not only against *Echinochloa oryzicola* which is a hard gramineous weed but also against broadleaf weeds such as *Monochoria vaginalis, Lindernia pyxidaria, Dopartium junceum* and *Rotala indica*, as well as Cyperaceous weeds including *Scirpus juncoides* and *Cyperus serotinus*.

DETAILED DESCRIPTION OF THE INVENTION

The compounds of the present invention are novel compounds represented by the formula I which differ in structure from known triazole compounds with respect to the portion denoted by A. Production of the compounds of the present invention will typically proceed as follows. A starting material, or a compound represented by the general formula II:

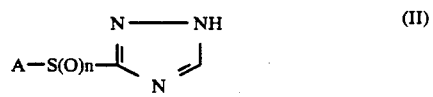

(where A and n have the same meanings as defined above) is reacted with a compound of the formula III:

where Y, $R_1$ and $R_2$ have the same meanings as defined above, and the reaction product is optionally oxidized with a suitable oxidizing agent to prepare a compound of the general formula I.

If the desired compound I is a sulfinyl compound (n=1) or a sulfonyl compound (n=2), a compound of formula II which has the S portion oxidized likewise may be used as the starting material. Alternatively, a compound of formula I which does not have the S portion oxidized may be first prepared and then oxidized as required. In the step of reacting oxidized or unoxidized compound II with compound III, compound II is reacted with 1–2 equivalents, preferably 1–1.2 equivalents, of compound III in a suitable solvent in the presence of at least 1 equivalent, preferably 1–2 equivalents, of a deprotonating agent. The reaction temperature is in the range of 0°–100° C., preferably 20°–70° C. Suitable deprotonating agents include inorganic bases such as sodium hydroxide, potassium hydroxide, sodium carbonate, sodium bicarbonate, and sodium hydride, and organic bases such as triethylamine and pyridine. Suitable solvents include: hydrocarbons such as benzene, toluene and xylene; halogenated hydrocarbons such as methylene chloride and chloroform; ethers such as diethyl ether, tetrahydrofuran and dioxane; ketones such as acetone and methyl ethyl ketone;

and others such as ethyl acetate, acetonitrile, dimethylformamide, pyridine, dimethyl sulfoxide, water, etc. These solvents may be used either on their own or as admixtures.

The oxidation step may be performed in a suitable solvent using an oxidizing agent. Useful oxidizing agents include inorganic oxidizing agents such as hydrogen peroxide, potassium permanganate and chromic acid, and organic oxidizing agents such as peracetic acid and m-chloroperbenzoic acid. Solvents that can be used include methylene chloride, chloroform, acetone, acetic acid, water, etc., which may be used either alone or in admixture. An appropriate reaction temperature is one between 0° and 50° C. inclusive but heating or cooling may be effected depending on the type of solvent used or on the progress of the reaction involved. Starting compounds of formula II are novel per se, except those in which A represents an unsubstituted phenyl group, a nitropheyl group, a nitroaminopheyl group, a dinitrophenyl group, a diaminophenyl group or an aminophenyl group, and such compounds are included within the scope of the present invention. They can be prepared by reacting a compound of the following formula IV:

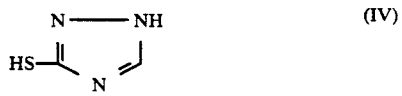

with a compound of the formula A-Z (where A has the same meaning as defined above, and Z is a halogen atom) in a suitable solvent. Alternatively, a compound A—NH$_2$ is dissolved in conc. HCl and NaNO$_2$ is added to form a diazonium salt solution, with a compound IV then being added to this solution.

Any solvent that is inert to the reactants may be used in preparing novel compounds II and those already described in connection with the preparation of compound I, including dimethylformamide, may be employed. The reaction temperature should be in the range of 20°-200° C., preferably 50°-150° C., when compound A-Z is used, and is in the range of 0°-100° C., preferably 0°-70° C., when compound A—NH$_2$ is used.

Compounds of the general formula I prepared by the methods described above cause little harm to crops and need only be used in low doses to exhibit marked herbicidal effects against *Echinochloa oryzicola* which is a hard gramineous weed. In addition, they exhibit strong herbicidal effects against broadleaf weeds (*Monochoria vaginalis, Lindernia pyxidaria, Dopartium junceum* and *Rotala indica*) and Cyperaceous weeds (e.g. *Scirpus juncoides* and *Cyperus serotinus*) at the early stage of their growth. If compounds of formula I are combined with one or more compounds selected from the group consisting of pyrazolate, pyrazoxyfen, benzofenap, bensulfuron methyl, pyrazosulfuron ethyl, bromobutide, clomeprop and CG-148, they will also exhibit superior herbicidal effects against fully grown broadleaf weeds and Cyperaceous weeds. These compounds (i.e. the group of known herbicides to be combined with compounds of formula I) are known to be effective against perennial weeds including broadleaf weeds and Cyperaceous weeds (see Japanese Patent Publication for Opposition Nos. 54-36648, 56-43455, 60-29328, 62-6705, 62-19402, and Japanese Patent Publication for Laying-Open Nos. 57-171904, 57-56452 and 59-122488). Among these compounds, the pyrazole compounds, i.e., pyrazolate, pyrazoxyfen and benzofenap, are effective against *Echinochloa oryzicola*, broadleaf weeds, *Cyperus serotinus* and *Sagittaria pygmaea* at the early stage of their growth, but are not satisfactorily effective against fully grown *Echinochloa oryzicola*. The sulfonyl urea compounds, i.e., bensulfuron methyl, pyrazosulfuron ethyl and CG-148, are effective against broadlead weeds, *Cyperus serotinus* and *Sagittaria pygmaea* even if they are used in a very low dose, but are not very effective against *Echinochloa oryzicola* unless used in a high dose which would then harm crops, too. Bromobutide is effective against broadleaf weeds, *Scirpus juncoides* and *Cyperus serotinus*, but not very effective against *Echinochloa oryzicola* or broadleaf weeds. Clomeprop is effective against broadleaf weeds, *Scirpus juncoides* and *Sagittaria pygmaea*, but not very effective against *Echinochloa oryzicola*. In short, the known herbicides have the disadvantage of either narrow activity spectra or inability to exhibit complete weed control in a low dose. Under these circumstances, the same or different herbicides have to be applied several times or in a high dose and this is undesirable not only from the viewpoint of labor and cost but also because such doses will lead to crop injury and high herbicide residues in the soil.

The present inventors conducted intensive studies in order to solve these problems of the conventional herbicides and found that surprising effects could be attained by using compounds of the general formula I either independently or in combination with the group of known herbicides. In the case of combined use, entirely unexpected synergistic effects can be accomplished: i.e., broad activity spectra are attained as compared with the scope of applications of individual herbicides; marked herbicidal effects are exhibited in a low dose without causing any injury to crops; and these effects last for an extended period of time.

The compounds in the group of known herbicides listed above may be synthesized by the methods described in the following patents:

Pyrazolate:

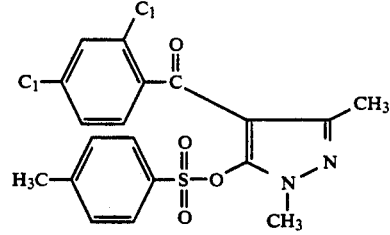

(Japanese Patent Publication for Opposition No. 54-36648) Pyrazoxyfen:

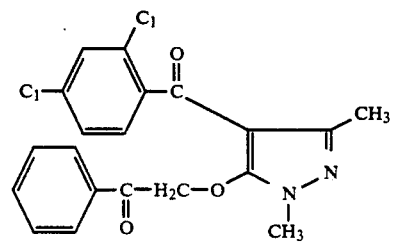

(Japanese Patent Publication for Opposition No. 60-29388) Benzofenap:

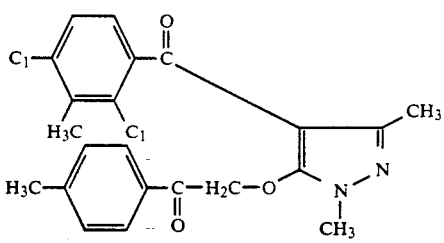

(Japanese Patent Publication for Opposition No. 62-19402) Bensulfuron methyl:

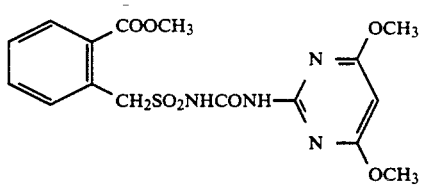

(Japanese Patent Publication for Opposition No. 62-6705)
Pyrazosulfuron ethyl:

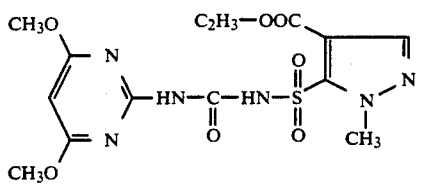

(Japanese Patent Publication for Laying-open No. 59-122488)
Bromobutide:

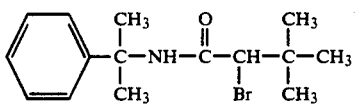

(Japanese Patent Publication for Opposition No. 56-43455) Chlomeprop:

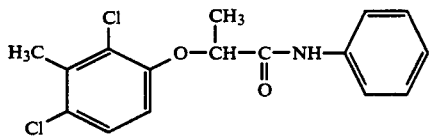

(Japanese Patent Publication for Laying-open. 57-171904) CG-148:

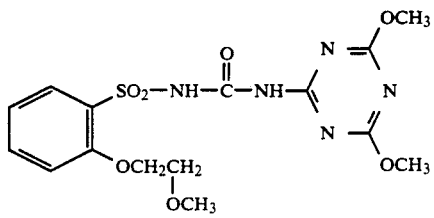

(Japanese Patent Publication for Laying-open No. 57-56452)

The herbicide combinations prepared in accordance with the present invention are combinations that have not yet been described in literature and, needless to say, no existing liternature refers to the unique potentiating effects of these combinations.

The synergistic effects of these combinations are exhibited over a broad range of mixing ratios and useful herbicides can be prepared by mixing one part by weight of compounds of the general formula I with 0.05-10 parts by weight of compounds in the group of known herbicides. The so prepared herbicides of the present invention will attain high activity by pre-emergence and/or post-emergence soil treatments.

The present invention is described hereinafter in greater detail with reference to examples.

The following Examples 1-6 relate to the preparation of compounds that are represented by formula II and which are used as starting materials for the synthesis of compounds of formula I.

EXAMPLE 1

Synthesis of 3-(2-Chloro-4-Trifluoromethylphenylthio)-1,2,4-Triazole

A sodium salt of 3-mercapto-1,2,4-triazole (80 g) is added to dimethylformamide (150 ml). To the resulting suspension, 3,4-dichlorobenzotrifluoride (101 g) is added and the mixture is stirred under reflux for 25 h. After cooling, water (500 ml) is added to the reaction solution, whereupon an oil separates. The separating oil is extracted with ethyl acetate and the extract is washed successively with 1 N HCl, water, 5% aqueous sodium bicarbonate and water, and dried with Mg SO$_4$. When the solvent is distilled off, an oil remains. Purification by silica gel chromatography (solvent: chloroform) gives the crystal of 3-(2-chloro-4-trifluorophenylthio)-1,2,4-triazole in an amount of 58.3 g: yield, 44.5%; m.p., 109°-110.5° C.

Elemental analysis for C$_9$H$_5$ClF$_3$N$_3$S (mw, 279.86):

|           | C     | H    | N     |
|-----------|-------|------|-------|
| Cal'd (%):| 38.65 | 1.80 | 15.03 |
| Found (%):| 38.55 | 1.20 | 15.02 |

EXAMPLE 2

Synthesis of 3-(3-Chlorophenylthio)-1,2,4-Triazole m-Chloroaniline (3.8 g) is dissolved in a mixture of conc. HCl (5 ml) and crushed ice (5 g) and held at 0° C. An aqueous solution (5 ml) of sodium nitrite (2.2 g) is poured slowly into the mixture so that the reaction temperature will not exceed 4° C. The resulting solution is added at 40°-50° C. to a solution consisting of a potassium salt of 3-mercapto-1,2,4-triazole (4.5 g) dissolved in water (30 ml) and the mixture is stirred at the same temperature for another 30 minutes.

After cooling, the reaction product is extracted with chloroform, washed with water, and dried with magnesium sulfate. After distilling off the solvent, the remaining oil is purified by silica gel chromatography (solvent: chloroform) to obtain an oil in an amount of 4.3 g; yield, 68%.

1H-NMR (CDCl$_3$) δ:7.2–7.6 (4H, m), 8.8 (1H, s), 12.0 (1H, br. s) Elemental analysis for C$_8$H$_6$ClN$_3$S (mw, 211.674):

|  | C | H | N |
|---|---|---|---|
| Cal'd (%): | 45.39 | 2.86 | 19.85 |
| Found (%): | 45.43 | 2.72 | 19.73 |

EXAMPLE 3

Synthesis of 3-(2-Chloro-4-Trifluoromethylphenylsulfonyl)-1,2,4-Triazole

Sulfuric acid (2N, 200 ml) is added to a solution of 3-(2-chloro-4-trifluoromethylphenylthio)-1,2,4-triazole (35 g) in acetone (300 ml). With the temperature held at 25° C. or below, a saturated aqueous solution of potassium permanganate (40 g) is added dropwise to start reaction. After the dropwise addition, the mixture is stirred at room temperature for another 2 h, followed by addition of a saturated aquous solution of sodium hydrogensulfite until the solution becomes colorless. The resulting crystal is recovered by filtration and dried. Recrystallization from ethylacetate produces a white crystal in an amount of 21.3 g; yield, 54.6%; m.p. 222°–223.5° C.

Elemental analysis for C$_9$H$_5$ClF$_3$N$_3$O$_2$S (mw, 311.68):

|  | C | H | N |
|---|---|---|---|
| Cal'd (%): | 34.68 | 1.62 | 13.48 |
| Found (%): | 34.90 | 1.72 | 13.61 |

EXAMPLE 4

Synthesis of 3-(Phenylthio)-1,2,4-Triazole

3-Amino-1,2,4-triazole (12 g) is dissolved in 40% sulfuric acid (26 ml), and with temperature held at 5° C. or below, a solution consisting of sodium nitrite (11.9 g) dissolved in water (36 ml) is added dropwise. Subsequently, a saturated aqueous solution of sodium acetate is added to adjust the pH of the mixture to 4–5. The resulting solution is added over 1.5 h under cooling with ice to a solution composed of thiophenol (11.6 ml), sodium hydroxide (4.72 g) and water (30 ml). The reaction is stirred at room temperature for 0.5 h, then at 40°–50° C. for 1.5 h. After the reaction, the resulting product is extracted with ethyl acetate, washed with water, and dried with magnesium sulfate. When the solvent is distilled off, an oil remains. When this is purified by silica gel chromatography (solvent: chloroform-2% methanol), an oil is produced in an amount of 12.88 g; yield, 64.9%.

1H-NMR data (CDCl$_3$) δ:7.0–7.5 (5H, m), 7.90 (1H, s), 13.1 (1H, br. s)

Elemental analysis for C$_8$H$_7$N$_3$S (mw, 177.234):

|  | C | H | N |
|---|---|---|---|
| Cal'd (%): | 54.22 | 3.98 | 23.71 |
| Found (%): | 54.38 | 3.78 | 23.69 |

EXAMPLE 5

Synthesis of 3-(2,6-Dimethylphenylthio)-1,2,4-Triazole

A 200-ml flask submerged in an ice bath is charged with conc. HCl (5 ml) and crushed ice (20 g), and 2,6-dimethylaniline (3.6 g) is added slowly with stirring. The resulting mixture is cooled at 0° C. and a cold aqueous solution consisting of sodium nitrite (2.2 g) dissolved in water (5 ml) is poured slowly so that the reaction temperature will not exceed 4° C. In a separate step, a potassium salt of 3-mercaptotriazole (4.5 g) is dissolved in water (50 ml) at 40°–50° C. and a preliminarily prepared diazonium salt solution is added to this aqueous solution through a dropping funnel. The resulting mixture is stirred at 50°–60° C. for an additional 30 minutes. After cooling to room temperature, the organic layer is extracted with chloroform, washed with water and dried with magnesium sulfate. The solvent is distilled off and the resulting crude crystal is recrystallized with a mixed solvent of ethyl acetate and n-hexane; m.p. 126°–127° C.; yield, 4.4 g (71%).

Elemental analysis for C$_{10}$H$_{11}$N$_3$S (mw, 205.288):

|  | C | H | N |
|---|---|---|---|
| Cal'd (%): | 58.51 | 5.40 | 20.47 |
| Found (%): | 58.40 | 5.51 | 20.56 |

EXAMPLE 6

Synthesis of 3-(2-Methyl-6-Ethylphenyl-Sulfonyl)-1,2,4-Triazole 3-(2-Methyl-6-ethylphenylthio)-1,2,4-triazole (21.9 g) is dissolved in acetic acid (120 ml) and heated to 70° C. with stirring. To the solution is added dropwise 35% hydrogen peroxide (50 ml). Then the resulting mixture is stirred at 100° C. for an additional 3 h. Thereafter the mixture is left to incubate overnight at room temperature. The resulting crystal is recovered by filtration and recrystallized from ethyl acetate; yield, 18 g (72%), m.p. 180°–181° C.

Elemental analysis for C$_{11}$H$_{13}$N$_3$O$_2$S (mw, 251.31):

|  | C | H | N |
|---|---|---|---|
| Cal'd (%): | 52.57 | 5.21 | 16.72 |
| Found (%): | 52.61 | 5.18 | 16.60 |

The following Examples 7–13 relate to the synthesis of compounds as final end products of the present invention.

EXAMPLE 7

Synthesis of 1-(Diethylcarbamoyl)-3-(2-nitrophenylthio)-1,2,4-Triazole (compound No. 67)

3-(2-Nitrophenylthio)-1,2,4-triazole (4 g) and diethyl carbamoyl chloride (2.71 g) are dissolved in acetone (50 ml) and potassium carbonate (5.5 g) is added, followed by reaction for 5 h under reflux with stirring. After cooling, water (100 ml) is added to the reaction solution, whereupon the crystal of the end product precipitates. After drying, the crystal is recrystallized from ethyl acetate/n-hexane to produce the titled compound, 1-(diethylcarbamoyl)-3-(2-nitrophenylthio)-1,2,4- triazole, in an amount of 5.08 g; yield, 87.8%; m.p. 101°–103° C.

Elemental analysis for $C_{13}H_{15}N_5O_3S$ (mw, 321.37):

|  | C | H | N |
|---|---|---|---|
| Cal'd (%): | 48.59 | 4.71 | 21.86 |
| Found (%): | 48.41 | 4.65 | 21.72 |

EXAMPLE 8

Synthesis of 1-(Diethylcarbamoyl)-3-(2-Chloro-4-Trifluoromethyl-Phenylsulfonyl)-1,2,4-Triazole (compound No. 20)

3-(2-Chloro-4-trifluoromethylphenylsulfonyl)-1,2,4-triazole (3.12 g) and diethyl carbamoyl chloride (1.62 g) are dissolved in pyridine (10 ml) and reaction is performed at 50° C. for 5 h. After completion of the reaction, water (50 ml) is added to the reaction solution and the reaction product is extracted twice with ethyl acetate (100 ml). The ethyl acetate layer is washed first with 1N HCl, then with water, and subsequently dried with magnesium sulfate. The dried product is concentrated to form a crystal. Recrystallization from benzene/n-hexane produces the titled compound, 1-(diethylcarbamoyl)-3-(2-chloro-4-trifluoromethylphenylsulfonyl)-1,2,4-triazole, in an amount of 3.80 g; yield, 92.5%; m.p. 105.5°–107° C.

Elemental analysis for $C_{14}H_{14}ClF_3N_4O_3S$ (mw, 410.82)

|  | C | H | N |
|---|---|---|---|
| Cal'd (%): | 35.08 | 3.44 | 13.64 |
| Found (%): | 35.15 | 3.41 | 13.58 |

EXAMPLE 9

Synthesis of 1-(Diethylcarbamoyl)-3-(2-Chloro-4-Trifluoromethyl-Phenylsulfinyl)-1,2,4-Triazole (compound No. 65)

1-(Diethylcarbamoyl)-3-(2-chloro-4-trifluoromethylphenylthio)-1,2,4-triazole (3.79 g) is dissolved in chloroform (100 ml). With the temperature held at 10° C. or below with ice water, m-chloro-perbenzoic acid (1.73 g) is added in small portions over a period of 10 minutes. Thereafter, reaction is performed at 10° C. for 2 h, then at room temperature for 10 h. The chloroform solution is washed twice with a 10% aqueous solution of potassium carbonate (100 ml), then washed with water, and dried with magnesium sulfate. When the solvent is distilled off, an oil remains. This is purified by silica gel chromatography (solvent 1:1 mixture of chloroform and n-hexane) to produce the titled compound, 1-(diethylcarbamoyl)-3-(2-chloro-4-trifluoromethylphenylsulfinyl)-1,2,4-triazole (2.7 g) as an oil; yield, 68.4%.

Elemental analysis for $C_{14}H_{14}ClF_3N_4O_2S$ (mw, 394.815):

|  | C | H | N |
|---|---|---|---|
| Cal'd (%): | 42.59 | 3.57 | 14.19 |
| Found (%): | 42.71 | 3.46 | 14.30 |

EXAMPLE 10

Synthesis of 1-(Diethylcarbamoyl)-3-(2-Chloro-4-Trifluoromethyl-Phenylsulfonyl)-1,2,4-Triazole (compound No. 20)

1-(Diethylcarbamoyl)-3-(2-chloro-4-trifluoromethylphenylthio)-1,2,4-triazole (3.79 g) is dissolved in chloroform (100 ml). With the temperature held at 10° C. or below with ice water, m-chloroperbenzoic acid (5 g) is added in small portions. Thereafter, reaction is performed at 10° C. for 2 h, then at room temperature for 10 h, and finally at an elevated temperature of 50° C. for 2 h. The chloroform solution is washed twice with a 10% aqueous solution of potassium carbonate and dried with magnesium sulfate. By distilling off the solvent, a crystal is obtained. Recrystallization from benzene/n-hexane produces the titled compound, 1-(diethylcarbamoyl)-3-(2-chloro-4-trifluoromethylphenylsulfonyl)-1,2,4-triazole, in an amount of 3.50 g; yield, 85.2%; m.p. 105.5°–107° C.

EXAMPLE 11

Synthesis of 1-(Diethylcarbamoyl)-3-(2,6-Dimethylphenylsulfonyl)-1,2,4-Triazole (compound No. 1)

3-(2,6-Dimethylphenylthio)-1,2,4-triazole (2 g) is dissolved in pyridine (50 ml) and diethyl carbamoyl chloride (1.4 g) is added dropwise to the solution. The mixture is stirred first at room temperature for 1 h, then at 70° C. for 2 h. Thereafter, pyridine is distilled off. The residue is extracted with chloroform and dried with magnesium sulfate to obtain the crude product of 1-(diethylcarbamoyl)-3-(2,6-dimethylphenylthio)-1,2,4-triazole. After cooling to 0° C., m-chloroperbenzoic acid (4 g) is added and the mixture is stirred at room temperature for 4 h. The resulting product is washed with a 10% aqueous solution of potassium carbonate and dried with magnesium sulfate. After distilling off the solvent, the residue is recrystallized with n-hexane/ethyl acetate; m.p. 111°–112° C.; yield, 2.4 g (72%).

Elemental analysis for $C_{15}H_{20}N_4O_3S$ (mw, 336.408):

|  | C | H | N |
|---|---|---|---|
| Cal'd (%): | 53.56 | 5.99 | 16.65 |
| Found (%): | 53.41 | 5.85 | 16.70 |

EXAMPLE 12

Synthesis of 1-(Diethylcarbamoyl)-3-(2,4,5-Trimethyl-6-Methoxyphenylsulfonyl)-1,2,4-Triazole (compound No. 167)

3-(2,4,5-Trimethyl-6-methoxyphenylthio)-1,2,4-triazole (2.5 g) is dissolved in pyridine (60 ml) and diethyl carbamoyl chloride (1.4 g) is added dropwise to the solution. The mixture is stirred at room temperature for 1 h, then at 70° C. for 2 h. After distilling off pyridine, the residue is extracted with chloroform and dried with magnesium sulfate to obtain a crude product of 1-(diethylcarbamoyl)-3-(2,4,5-trimethyl-6-methoxyphenylthio)-1,2,4-triazole. This crude product is cooled to 0° C. and m-chloroperbenzoic acid (4 g) is added, followed by stirring at room temperature for 2 h and at 60° C. for 2 h. Subsequently, the resulting product is washed with a 10% aqueous solution of potassium carbonate and dried with magnesium sulfate. After distilling off the solvent, the residue is recrystallized from n-hexane/ethyl acetate; yield, 2.6 g (74%); m.p. 138°–139° C.

Elemental analysis for $C_{17}H_{24}N_4O_2S$ (mw, 348.471):

|  | C | H | N |
|---|---|---|---|
| Cal'd (%): | 58.60 | 6.94 | 16.08 |
| Found (%): | 58.52 | 6.90 | 15.95 |

EXAMPLE 13

Synthesis of 1-(Diethylcarbamoyl)-3-(2-Methyl-6-Ethylphenylsulfonyl)-1,2,4-Triazole (compound No. 10)

3-(2-Methyl-6-ethylphenylsulfonyl)-1,2,4-triazole (25.1 g) and diethylcabamoyl chloride (14 g) are dissolved in acetone (200 ml) and potassium carbonate (14 g) is added, followed by reaction for 3 h under reflux with stirring. After completion of the reaction, the resulting precipitate is removed by filtration. The residual mother liquid is concentrated to obtain a crude roduct of the titled comound. This is purified by silica gel chromatography (solvent: n-hexane-ethyl acetate) to give an oil.

NMR data δ: 1.10–1.41(9H,m), 2.67(3H,s), 3.12(2H,q), 3.48(4H,q), 7.02–7.45(3H,m), 8.72(1H,s)

When left to incubated in the cold, a crystal is given, and this is followed by recrystallization from n-hexane-ethyl acetate (1:1); m.p. 82°–83° C.

Elemental analysis for $C_{16}H_{22}N_4O_3S$ (mw, 350.44):

|  | C | H | N |
|---|---|---|---|
| Cal'd (%): | 54.84 | 6.33 | 15.99 |
| Found (%): | 54.91 | 6.25 | 15.82 |

The compounds of general formula I listed in Table 1 below can be synthesized by similar procedures from the corresponding starting materials.

TABLE 1

| Compound No. | $R_1$ | $R_2$ | n | Xm | Physical data |
|---|---|---|---|---|---|
| 1 | $C_2H_5$ | $C_2H_5$ | 2 | 2,6-$(CH_3)_2$ | m.p. 111–112° C. |
| 2 | $C_2H_5$ | $C_2H_5$ | 2 | 2,3-$(CH_3)_2$ | m.p. 92–93° C. |
| 3 | $C_2H_5$ | $C_2H_5$ | 2 | 2,4,6-$(CH_3)_3$ | m.p. 113–114° C. |
| 4 | $C_2H_5$ | $C_2H_5$ | 2 | 2-Cl, 3-$CH_3$ | m.p. 154–155° C. |
| 5 | $C_2H_5$ | $C_2H_5$ | 2 | 2-Cl, 4-$CH_3$ | m.p. 132–133° C. |
| 6 | $C_2H_5$ | $C_2H_5$ | 2 | 2-Cl, 6-$CH_3$ | m.p. 105–106° C. |
| 7 | $C_2H_5$ | $C_2H_5$ | 2 | 2,6-$Cl_2$, 3-$CH_3$ | m.p. 137–138° C. |
| 8 | $C_2H_5$ | $C_2H_5$ | 2 | 5-Cl, 2-$OCH_3$ | m.p. 131–132° C. |
| 9 | $C_2H_5$ | $C_2H_5$ | 2 | 2-$CH_3$, 6-$OC_3H_7$-i | oil, NMR δ: 1.00–1.32(12H, m)2.76(3H, s) 3.54(4H, q)4.52(1H, m) 6.70–7.00(2H, m)7.50(1H, m) 8.90(1H, s) |
| 10 | $C_2H_5$ | $C_2H_5$ | 2 | 2-$CH_3$, 6-$C_2H_5$ | oil, NMR δ: 1.10–1.41(9H, m)2.67(3H, s) 3.12(2H, q)3.48(4H, q) 7.02–7.45(3H, m)8.72(1H, s) |
| 11 | $C_2H_5$ | $C_2H_5$ | 2 | 4-Cl, 2-$CH_3$ | m.p. 99–100° C. |
| 12 | $C_2H_5$ | $C_2H_5$ | 2 | 2-Cl, 5-$CH_3$ | m.p. 150–151° C. |
| 13 | $C_2H_5$ | $C_2H_5$ | 2 | 3-Cl, 2-$OCH_3$ | m.p. 124–125° C. |
| 14 | $C_2H_5$ | $C_2H_5$ | 2 | 2-$OCH_3$ | NMR δ: 1.13(6H, t)3.3–3.6(4h, q)3.68 (3H, s)6.9–8.1(4H, m)8.27(1H, s) |
| 15 | $C_2H_5$ | $C_2H_5$ | 2 | 2,6-$Cl_2$ | m.p. 154–155° C. |
| 16 | $C_2H_5$ | $C_2H_5$ | 2 | 2,6-$F_2$ | m.p. 144–145° C. |
| 17 | $C_2H_5$ | $C_2H_5$ | 2 | 2-Cl, 4-$NO_2$ | m.p. 110–115° C. |
| 18 | $C_2H_5$ | $C_2H_5$ | 2 | 4-Cl | m.p. 103–104° C. |
| 19 | $C_2H_5$ | $C_2H_5$ | 2 | 2,4-$Cl_2$ | NMR δ: 1.16(6H, t)3.84(4H, q) 7.1–7.6(3H, m)8.7(1H, s) |
| 20 | $C_2H_5$ | $C_2H_5$ | 2 | 2-Cl, 4-$CF_3$ | m.p. 105.5–107° C. |
| 21 | $C_2H_5$ | $C_2H_5$ | 2 | 2-Cl, 5-$CF_3$ | m.p. 72–73° C. |
| 22 | $C_2H_5$ | $C_2H_5$ | 2 | 3-$CF_3$ | NMR δ: 1.05(6H, t)3.45(4H, q) 7.2–7.6(4H, m)8.70(1H, s) |
| 23 | $C_2H_5$ | $C_2H_5$ | 2 | 2-$C_3H_7$-i | m.p. 98–99° C. |
| 24 | $C_2H_5$ | $C_2H_5$ | 2 | 2-Br | m.p. 102.0° C. |
| 25 | $C_2H_5$ | $C_2H_5$ | 2 | 2$CH_3$ | m.p. 110.5° C. |
| 26 | $C_2H_5$ | $C_2H_5$ | 2 | 3-$C_2H_5$ | m.p. 82.5° C. |
| 27 | $C_2H_5$ | $C_2H_5$ | 2 | 4-$C_2H_5$ | m.p. 86.0° C. |
| 28 | $C_2H_5$ | $C_2H_5$ | 2 | 3,4-$OCH_2O$—* | m.p. 109.5° C. |
| 29 | $C_2H_5$ | $C_2H_5$ | 2 | 2-CH(OH)—⟨phenyl⟩-4-Cl 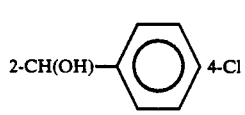 | m.p. 138–139° C. |
| 30 | $C_2H_5$ | $C_2H_5$ | 2 | 2-$CH_3$, 3-Cl, 6-C(O) $C_3H_7$-i | oil, NMR δ: 1.10–1.40(9H, m)2.64(3H, s) 3.0–4.2(8H, m)7.11(1H, d)7.69(1H, d) 8.91(1H, s) |
| 31 | $C_2H_5$ | $C_2H_5$ | 2 | 5-Cl, 2-$CH_3$ | m.p. 121–122° C. |
| 32 | $C_2H_5$ | $C_2H_5$ | 2 | 2,5-$(CH_3)_2$ | m.p. 77–78° C. |
| 33 | $C_2H_5$ | $C_2H_5$ | 2 | 2,6-$Br_2$ | m.p. 122–123° C. |
| 34 | $C_2H_5$ | $C_2H_5$ | 2 | 2-⟨phenyl⟩ 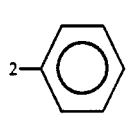 | m.p. 176.5° C. |

TABLE 1-continued

| Compound No. | R₁ | R₂ | n | Xm | Physical data |
|---|---|---|---|---|---|
| 35 | $C_2H_5$ | $C_2H_5$ | 2 | 3,5-$Cl_2$ 6-$OC_3H_7$-i | oil, NMR δ: 1.07–1.30(12H, m)3.49(4H, q) 5.08(1H, m)7.09(1H, d)8.01(1H, d) 8.81(1H, s) |
| 36 | $C_2H_5$ | $C_2H_5$ | 2 | 6Cl 2-CH(OH)—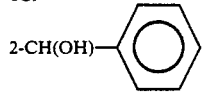 | oil, NMR δ: 1.18(6H, t)3.46(4H, q) 4.01(1H, d)7.10–7.50(9H, m) 8.78(1H, s) |
| 37 | $C_2H_5$ | $C_2H_5$ | 2 | 2,6-$Cl_2$ 4-$C_4H_9$-t | oil, NMR δ: 1.15(6H, t)1.75(9H, s) 3.43(4H, q)7.40(2H, s)8.82(1H, s) |
| 38 | $C_2H_5$ | $C_2H_5$ | 2 | 2-Cl, 4-$C_4H_9$-t | m.p. 82–83° C. |
| 39 | $C_2H_5$ | $C_2H_5$ | 2 | 2,3-$CH_2$—$CH_2$—$CH_2$—$CH_2$—** | oil, NMR δ: 1.11(6H, t)1.52–1.75(4H, m) 2.65–3.05(4H, m)3.42(4H, q)7.15– 7.34(2H, m)7.85–8.01(1H, m) 8.71(1H, s) |
| 40 | $C_2H_5$ | $C_2H_5$ | 2 | 3-Cl, 2-$CH_3$, 6-CH(OH)—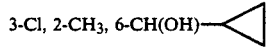 | m.p. 88–89° C. |
| 41 | $C_2H_5$ | $C_2H_5$ | 2 | 2,3-CH=CH—CH=CH—*** | m.p. 117–118° C. |
| 42 | $C_2H_5$ | $C_2H_5$ | 2 | 2-$CH_2$—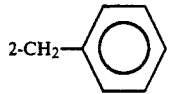 | m.p. 87–88° C. |
| 43 | $C_2H_5$ | $C_2H_5$ | 2 | 2-$CH_3$, 5-$C_3H_7$-i | oil, NMR δ: 1.13–1.83(12H, m)2.18(3H, s) 3.00(1H, m)3.54(4H, q) 7.12–8.10(3H, m)8.82(1H, s) |
| 44 | $C_2H_5$ | $C_2H_5$ | 2 | 2-CH(OH)—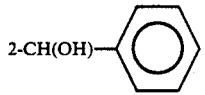 | oil, NMR δ: 1.12(6H, t)3.38(4H, q) 4.04(1H, d)6.94–7.46(9H, m) 8.12(1H, m)8.63(1H, s) |
| 45 | $C_2H_5$ | $C_2H_5$ | 2 | 2-O—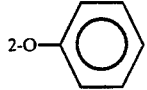 | oil, NMR δ: 1.13(6H, t)3.39(1H, q) 6.60–7.60(8H, m)8.06–8.19(1H, m) 8.62(1H, s) |
| 46 | $C_2H_5$ | $C_2H_5$ | 2 | 2,5-$Cl_2$ 3-$COOC_2H_5$ | oil, NMR δ: 1.14–1.60(9H, m)3.53(4H, q) 4.42(2H, q)8.47(1H, d)8.71(1H, d) 8.85(1H, s) |
| 47 | $C_2H_5$ | $C_2H_5$ | 2 | 2-F | m.p. 91.5° C. |
| 48 | $C_2H_5$ | $C_2H_5$ | 2 | 4-$C_3H_7$-n | NMR δ: 0.95(3H, t)1.26(6H, t) 1.16–2.0(2H, m)2.65(2H, t) 3.51(4H, q)7.26(2H, d)7.88(2H, d) 8.73(1H, s) |
| 49 | $C_2H_5$ | $C_2H_5$ | 2 | 4-Cl, 2-$CF_3$ | NMR δ: 1.15(6H, t)3.48(4H, q) 7.65–8.0(2H, m)8.45(1H, d) 8.80(1H, s) |
| 50 | $C_2H_5$ | $C_2H_5$ | 2 | 3-Cl, 4-$CF_3$ | m.p. 81.0° C. |
| 51 | $C_2H_5$ | $C_2H_5$ | 2 | 2-$NH_2$, 6-Cl | m.p. 139.5° C. |
| 52 | $C_2H_5$ | $C_2H_5$ | 2 | 2-Cl | m.p. 84–85° C. |
| 53 | $C_2H_5$ | $C_2H_5$ | 2 | 3-Cl, 2-$CH_3$ | m.p. 151–152° C. |
| 54 | $C_2H_5$ | $C_2H_5$ | 2 | 3-$COOC_2H_5$ | oil, NMR δ: 1.14–1.62(9H, m)3.52(4H, q) 4.40(2H, q)7.70(1H, m) 8.21–8.45(2H, m)8.69(1H, m) 8.87(1H, s) |
| 55 | $C_2H_5$ | $C_2H_5$ | 2 | 6-Cl, 2,3-$(CH_3)_2$ | m.p. 135–136° C. |
| 56 | $C_2H_5$ | $C_2H_5$ | 2 | 2,4-$Cl_2$, 3-$CH_3$ | m.p. 154–155° C. |
| 57 | $C_2H_5$ | $C_2H_5$ | 2 | 2-$CF_3$ | oil, NMR δ: 1.18(6H, t)3.47(4H, q) 7.10–7.95(3H, m)8.40–8.54(1H, m) 8.73(1H, s) |
| 58 | $C_2H_5$ | $C_2H_5$ | 2 | 2-Cl, 3-$COOCH_3$, 6-$CH_3$ | m.p. 111–2° C. |
| 59 | $C_2H_5$ | $C_2H_5$ | 2 | 2-$CH_3$, 3-$COOC_2H_5$ | oil, NMR δ: 1.10–1.49(9H, m)2.36(3H, s) 3.49(4H, q)4.36(2H, q)7.47(1H, m) 7.97–8.08(1H, m)8.30–8.42(1H, m) 8.86(1H, s) |
| 60 | $C_2H_5$ | $C_2H_5$ | 2 | 2-Cl, 5-$COOCH_3$ | m.p. 90–91° C. |
| 61 | $C_2H_5$ | $C_2H_5$ | 2 | 2-$CH_3$, 3-$OH_3$ | m.p. 154–155° C. |
| 62 | $C_2H_5$ | $C_2H_5$ | 2 | 2-$OCH_3$, 5-$CH_3$ | m.p. 146–147° C. |
| 63 | $C_2H_5$ | $C_2H_5$ | 2 | 2,5-$(OCH_3)_2$ | NMR δ: 1.25(6H, t)3.50(4H, q)3.68(3H, s) |

TABLE 1-continued

| Compound No. | R₁ | R₂ | n | Xm | Physical data |
|---|---|---|---|---|---|
| | | | | | 3.80(3H, s)6.90–7.30(2H, m)7.52–7.59(1H, m)8.57(1H, s) |
| 64 | C₂H₅ | C₂H₅ | 2 | 2-CH₃, 6-OCH₃ | m.p. 125–126° C. |
| 65 | C₂H₅ | C₂H₅ | 1 | 2-Cl, 4-CF₃ | NMR δ: 1.19(6H, t)3.3–3.7(4H, q) 7.5–8.4(3H, s, d)8.82(1H, s) |
| 66 | C₂H₅ | C₂H₅ | 0 | H | NMR δ: 1.11(6H, t)3.3–3.6(4H, q) 7.2–7.7(5H, m)8.71(1H, s) |
| 67 | C₂H₅ | C₂H₅ | 0 | 2-NO₂ | m.p. 101–103° C. |
| 68 | C₂H₅ | C₂H₅ | 0 | 2-NO₂, 4-CF₃ | m.p. 113–104° C. |
| 69 | C₂H₅ | C₂H₅ | 0 | 2-NO₂, 6-Cl | m.p. 79.0° C. |
| 70 | C₂H₅ | C₂H₅ | 0 | 4-Cl | NMR δ: 1.15(ppm)(6H, t)3.50(4H, q) 7.2–7.6(4H, m)8.77(1H, s) |
| 71 | C₂H₅ | C₂H₅ | 0 | 2,6-Cl₂ | m.p. 74–75° C. |
| 72 | C₂H₅ | C₂H₅ | 0 | 2-Cl, 5-CF₃ | NMR δ: 1.15(6H, t)3.47(4H, q) 7.3–7.9(3H, m)8.78(1H, s) |
| 73 | C₂H₅ | C₂H₅ | 0 | 2,3-(CH₃)₂ | m.p. 92–93° C. |
| 74 | C₂H₅ | n-C₃H₇ | 2 | H | m.p. 71–74° C. |
| 75 | C₂H₅ | n-C₃H₇ | 2 | 2-NO₂ | NMR δ: 0.76(3H, t)1.12(3H, t) 1.20–1.90(2H, m)3.10–3.70(4H, m) 7.60–7.90(3H, m)8.10–8.45(1H, m) 8.68(1H, s) |
| 76 | C₂H₅ | n-C₃H₇ | 2 | 2-Cl, 4-NO₂ | NMR δ: 0.60(3H, t)0.97(3H, t) 1.0–1.70(2H, m)2.90–3.60(4H, m) 8.0–8.40(3H, m)8.60(1H, s) |
| 77 | C₂H₅ | n-C₃H₇ | 2 | 4-NO₂, 3-CF₃ | m.p. 88–91° C. |
| 78 | C₂H₅ | n-C₃H₇ | 2 | 2-Cl, 4-CF₃ | m.p. 79–82° C. |
| 79 | C₂H₅ | n-C₃H₇ | 2 | 2-CF₃ | m.p. 100–102° C. |
| 80 | C₂H₅ | n-C₃H₇ | 2 | 4-CF₃ | m.p. 76–77° C. |
| 81 | C₂H₅ | n-C₃H₇ | 2 | 2-Br | m.p. 98.5° C. |
| 82 | C₂H₅ | n-C₃H₇ | 2 | 2-CH₃ | NMR δ: 0.89(3H, t)1.24(3H, t) 1.25–1.95(2H, m)2.65(3H, s) 3.15–3.85(4H, m)7.05–7.65(3H, m) 7.95–8.20(1H, m)8.74(1H, s) |
| 83 | C₂H₅ | n-C₃H₇ | 2 | 3,4-OCH₂O—* | NMR δ: 0.95(3H, t)1.30(3H, t)1.35–2.05 (2H, m)3.20–3.80(4H, m)6.05(2H, s) 6.85(1H, d)7.35(1H, d)7.57(1H, d, d) 8.75(1H, s) |
| 84 | C₂H₅ | n-C₃H₇ | 2 | 2-F | m.p. 81.5° C. |
| 85 | C₂H₅ | n-C₃H₇ | 2 | 3-Cl, 4-CF₃ | NMR δ: 0.92(3H, t)1.28(3H, t) 1.20–2.0(2H, m)3.25–4.0(4H, m) 7.80–8.40(3H, m)8.90(1H, s) |
| 86 | C₂H₅ | n-C₃H₇ | 2 | 2-Cl | m.p. 82–83° C. |
| 87 | C₂H₅ | n-C₃H₇ | 2 | 2,3-(CH₃)₂ | m.p. 108–109° C. |
| 88 | C₂H₅ | n-C₃H₇ | 2 | 2,6-(CH₃)₂ | m.p. 115–116° C. |
| 89 | C₂H₅ | n-C₃H₇ | 1 | 2-Cl, 4-CF₃ | NMR δ: 0.7–1.9(8H, t, t, q)3.3–3.7(4H, m) 7.6–8.4(3H, s, d)8.83(1H, s) |
| 90 | C₂H₅ | n-C₃H₇ | 0 | 2-NO₂ | NMR δ: 0.76(3H, t)1.12(3H, t)1.20–1.90 (2H, m)3.10–3.70(4H, m)7.0–7.50 (3H, m)7.85–8.15(1H, m)8.72(1H, s) |
| 91 | C₂H₅ | n-C₃H₇ | 0 | 2-NO₂, 4-CF₃ | m.p. 81.0° C. |
| 92 | C₂H₅ | n-C₃H₇ | 0 | 2-CF₃ | oil, NMR δ: 0.78(3H, t)1.09(3H, t) 1.3–1.9(2H, m)3.2–3.7(4H, m) 7.3–7.8(4H, m)8.71(1H, s) |
| 93 | C₂H₅ | ▷ | 0 | 2-NO₂ | NMR δ: 0.40–1.0(4H, m)1.30(3H, t) 2.95–3.40(1H, m)3.62(2H, q) 7.77–8.10(3H, m)8.35–8.70(1H, m) 8.74(1H, s) |
| 94 | n-C₃H₇ | n-C₃H₇ | 2 | H | m.p. 61–63° C. |
| 95 | n-C₃H₇ | n-C₃H₇ | 2 | 2-NO₂ | NMR δ: 0.86(6H, t)1.30–2.05(4H, m) 3.20–3.75(4H, t)7.75–8.10(3H, m) 8.30–8.70(1H, m)8.81(1H, s) |
| 96 | n-C₃H₇ | n-C₃H₇ | 2 | 4-NO₂ | m.p. 117–118° C. |
| 97 | n-C₃H₇ | n-C₃H₇ | 2 | 2-Cl, 6-NO₂ | m.p. 133.5° C. |
| 98 | n-C₃H₇ | n-C₃H₇ | 2 | 4-NO₂, 3-CF₃ | m.p. 109–111° C. |
| 99 | n-C₃H₇ | n-C₃H₇ | 2 | 2-Cl | m.p. 99–101° C. |
| 100 | n-C₃H₇ | n-C₃H₇ | 2 | 2-Cl, 4-CF₃ | m.p. 83.5–84.5° C. |
| 101 | n-C₃H₇ | n-C₃H₇ | 2 | 2-CF₃ | m.p. 87–90° C. |
| 102 | n-C₃H₇ | n-C₃H₇ | 2 | 4-CF₃ | m.p. 61–63° C. |
| 103 | n-C₃H₇ | n-C₃H₇ | 2 | 4-CH₃ | m.p. 62–63° C. |
| 104 | n-C₃H₇ | n-C₃H₇ | 2 | 4-Cl, 2-NO₂ | m.p. 125.5° C. |
| 105 | n-C₃H₇ | n-C₃H₇ | 0 | H | oil, NMR δ: 0.76(6H, t)1.1–1.8(4H, m) 3.1–3.5(4H, m)7.1–7.6(5H, m)8.63 (1H, s) |
| 106 | n-C₃H₇ | n-C₃H₇ | 0 | 2-NO₂ | m.p. 68.0° C. |
| 107 | n-C₃H₇ | n-C₃H₇ | 0 | 2-NO₂, 4-CF₃ | m.p. 86.0° C. |
| 108 | n-C₃H₇ | n-C₃H₇ | 0 | 4-Cl, 2-NO₂ | m.p. 78.0° C. |
| 109 | n-C₃H₇ | n-C₃H₇ | 0 | 2-Cl, 6-NO₂ | NMR δ: 0.30–0.90(6H, m)0.90–1.70(4H, m) 2.90–3.45(4H, m)7.0–7.60(3H, m) |

TABLE 1-continued

| Compound No. | $R_1$ | $R_2$ | n | Xm | Physical data |
|---|---|---|---|---|---|
| | | | | | 8.40(1H, s) |
| 110 | i-$C_3H_7$ | i-$C_3H_7$ | 2 | 2-Cl, 4-$CF_3$ | m.p. 150–152° C. |
| 111 | $CH_2CH=CH_2$ | $CH_2CH=CH_2$ | 2 | H | m.p. 48–50° C. |
| 112 | $CH_2CH=CH_2$ | $CH_2CH=CH_2$ | 2 | 2-$NO_2$ | NMR δ: 4.0(4H, br.d)4.70–6.10(6H, m) 7.55–7.90(3H, m)8.10–8.45(1H, m) 8.63(1H, s) |
| 113 | $CH_2CH=CH_2$ | $CH_2CH=CH_2$ | 2 | 4-$NO_2$ | m.p. 91–92° C. |
| 114 | $CH_2CH=CH_2$ | $CH_2CH=CH_2$ | 2 | 2-$NO_2$, 4-$CF_3$ | m.p. 87.5° C. |
| 115 | $CH_2CH=CH_2$ | $CH_2CH=CH_2$ | 2 | 4-Cl, 2-$NO_2$ | m.p. 95.0° C. |
| 116 | $CH_2CH=CH_2$ | $CH_2CH=CH_2$ | 2 | 6-Cl, 2-$NO_2$ | m.p. 133.0° C. |
| 117 | $CH_2CH=CH_2$ | $CH_2CH=CH_2$ | 2 | 2-Cl, 4-$NO_2$ | m.p. 118–9° C. |
| 118 | $CH_2CH=CH_2$ | $CH_2CH=CH_2$ | 2 | 4-$NO_2$, 3-$CF_3$ | m.p. 90–3° C. |
| 119 | $CH_2CH=CH_2$ | $CH_2CH=CH_2$ | 2 | 2-Cl | m.p. 69–72° C. |
| 120 | $CH_2CH=CH_2$ | $CH_2CH=CH_2$ | 2 | 4-Cl | oil, NMR δ: 4.03(4H, d)4.9–6.1(6H, m) 7.3–8.1(4H, m)8.80(1H, s) |
| 121 | $CH_2CH=CH_2$ | $CH_2CH=CH_2$ | 2 | 2-Cl, 4-$CF_3$ | m.p. 76.5° C. |
| 122 | $CH_2CH=CH_2$ | $CH_2CH=CH_2$ | 2 | 2-$CF_3$ | m.p. 71–74° C. |
| 123 | $CH_2CH=CH_2$ | $CH_2CH=CH_2$ | 2 | 3-$CF_3$ | m.p. 70–72° C. |
| 124 | $CH_2CH=CH_2$ | $CH_2CH=CH_2$ | 2 | 4-$CF_3$ | m.p. 87–88° C. |
| 125 | $CH_2CH=CH_2$ | $CH_2CH=CH_2$ | 2 | 4-$CH_3$ | m.p. 91–92° C. |
| 126 | $CH_2CH=CH_2$ | $CH_2CH=CH_2$ | 2 | 4-$OC_2H_5$ | oil, NMR δ: 1.35(3H, t)3.77–4.10(6H, m) 4.83–6.13(6H, m)7.31(2H, d) 7.91(2H, d)8.20(1H, s) |
| 127 | $CH_2CH=CH_2$ | $CH_2CH=CH_2$ | 2 | 3-$C_2H_5$ | NMR δ: 1.20(3H, t)2.65(2H, q)4.0(4H, d) 4.75–6.05(6H, m)6.90–7.45(4H, m) 8.60(1H, s) |
| 128 | $CH_2CH=CH_2$ | $CH_2CH=CH_2$ | 2 | 4-$C_2H_5$ | NMR δ: 1.28(3H, t)2.74(2H, q)4.12(4H, d) 4.83–6.13(6H, m)7.31(2H, d) 7.91(2H, d)8.73(1H, s) |
| 129 | $CH_2CH=CH_2$ | $CH_2CH=CH_2$ | 2 | 4-$C_3H_7$-n | NMR δ: 0.92(3H, t)1.20–2.0(2H, m) 2.70(2H, t)4.12(4H, d) 4.95–6.20(6H, m)7.37(2H, d) 8.00(2H, d)8.82(1H, d) |
| 130 | $CH_2CH=CH_2$ | $CH_2CH=CH_2$ | 0 | 2-$NO_2$ | m.p. 65.5° C. |
| 131 | $CH_2CH=CH_2$ | $CH_2CH=CH_2$ | 0 | 4-$CF_3$, 2-$NO_2$ | m.p. 84.5° C. |
| 132 | $CH_2CH=CH_2$ | $CH_2CH=CH_2$ | 0 | 4-Cl, 2-$NO_2$ | m.p. 86.0° C. |
| 133 | $CH_2CH=CH_2$ | $CH_2CH=CH_2$ | 0 | 6-Cl, 2-$NO_2$ | m.p. 81.0° C. |
| 134 | $CH_2CH=CH_2$ | $CH_2CH=CH_2$ | 0 | 2-Cl | oil, NMR δ: 4.03(4H, d)4.9–6.1(6H, m) 7.1–7.8(4H, m)8.74(1H, s) |
| 135 | $CH_2CH=CH_2$ | $CH_2CH=CH_2$ | 0 | 4-Cl | oil, NMR δ: 4.04(4H, d)4.9–6.2(6H, m) 7.1–7.7(4H, m)8.75(1H, s) |
| 136 | $CH_2CH=CH_2$ | $CH_2CH=CH_2$ | 0 | 2-Cl, 4-$CF_3$ | NMR δ: 4.08(4H, br.d)4.90–6.20(6H, m) 7.30–7.85(3H, m)8.82(1H, s) |
| 137 | $CH_2CH=CH_2$ | $CH_2CH=CH_2$ | 0 | 2-$CF_3$ | oil, NMR δ: 3.99(4H, d)4.8–6.1(6H, m) 7.3–7.8(1H, m)8.71(1H, s) |
| 138 | $CH_2CH=CH_2$ | $CH_2CH=CH_2$ | 0 | 3-$CH_3$ | m.p. 63–64° C. |
| 139 | $CH_2CH=CH_2$ | $CH_2CH=CH_2$ | 0 | 4-$CF_3$ | oil, NMR δ: 4.02(4H, d)4.9–6.1(6H, m) 7.51(4H, m)8.69(1H, s) |
| 140 | $CH_2CH=CH_2$ | $CH_2CH=CH_2$ | 0 | 4-$CH_3$ | oil, NMR δ: 2.01(3H, s)3.73(4H, d) 4.6–5.8(6H, m)6.6–7.3(4H, m) 8.47(1H, s) |
| 141 | $CH_2CH=CH_2$ | $CH_2CH=CH_2$ | 0 | 3-$C_2H_5$ | NMR δ: 1.20(3H, t)2.65(2H, q)4.0(4H, d) 4.75–6.05(6H, m)6.90–7.45(4H, m) 8.60(1H, s) |
| 142 | $CH_2CH=CH_2$ | $CH_2CH=CH_2$ | 0 | 4-$C_2H_5$ | NMR δ: 1.26(3H, t)2.65(2H, q)4.08(4H, m) 4.85–6.10(6H, m)7.15(2H, d) 7.50(2H, d)8.68(1H, s) |
| 143 | (pyrrolidinyl, $R_1$–$R_2$ = N-ring, 5-membered) | | 2 | 2-Cl, 4-$CF_3$ | m.p. 146–147° C. |
| 144 | (pyrrolidinyl, $R_1$–$R_2$ = N-ring, 5-membered) | | 0 | 2-Cl, 4-$CF_3$ | NMR δ: 1.8–2.1(4H, m)3.5–4.0(4H, m) 7.4–7.7(3H, m)8.88(1H, s) |
| 145 | (piperidinyl, $R_1$–$R_2$ = N-ring, 6-membered) | | 2 | 2-Cl, 4-$CF_3$ | m.p. 128–130° C. |
| 146 | (piperidinyl, $R_1$–$R_2$ = N-ring, 6-membered) | | 2 | 4-Cl, 2-$NO_2$ | m.p. 134.0° C. |

TABLE 1-continued

| Compound No. | R₁ | R₂ | n | Xm | Physical data |
|---|---|---|---|---|---|
| 147 | | piperidino | 0 | 2-Cl, 4-CF₃ | NMR δ: 1.5–1.9(6H, m)3.6–3.9(4H, m) 7.5–7.7(3H, m)8.79(1H, s) |
| 148 | | piperidino | 0 | 2-NO₂ | m.p. 84.0° C. |
| 149 | | piperidino | 0 | 2-NO₂, 4-CF₃ | m.p. 161.0° C. |
| 150 | | piperidino | 2 | 2-NO₂ | m.p. 104.0° C. |
| 151 | | piperidino | 2 | 2-Cl, 4-CF₃ | m.p. 95–95.5° C. |
| 152 | | piperidino | 0 | 2-Cl, 4-CF₃ | NMR δ: 1.5–2.2(8H, m)3.6–4.0(4H, m) 7.5–7.9(3H, m)8.94(1H, s) |
| 153 | CH₂CCH | CH₂CCH | 0 | 2-Cl, 6-NO₂ | m.p. 125.0° C. |
| 154 | C₂H₅ | C₂H₅ | 2 | 2,6-(C₂H₅)₂ | oil, NMR δ: 1.08–1.39(12H, m) 2.95–3.68(8H, m)7.05–7.55(3H, m) 8.78(1H, s) |
| 155 | C₂H₅ | C₂H₅ | 2 | 2-CH₃, 6-i-C₃H₇ | oil, NMR δ: 1.11–1.32(12H, m), 2.73(3H, s)3.46(4H, q)4.19(1H, m) 6.95–7.39(3H, m)8.74(1H, s) |
| 156 | C₂H₅ | C₂H₅ | 2 | 2,6-(OCH₃)₂, 4-CH₃ | m.p. 141–142° C. |
| 157 | C₂H₅ | C₂H₅ | 2 | 2,6-(CH₃)₂, 4-Br | m.p. 124–125° C. |
| 158 | C₂H₅ | C₂H₅ | 2 | 2,6-(CH₃)₂, 4-OCH₃ | oil, NMR δ: 1.20(6H, t)2.34(3H, d) 2.75(3H, d)8.67(1H, s)3.50(4H, q) 3.58(3H, s)6.55–6.70(2H, m) |
| 159 | C₂H₅ | n-C₃H₇ | 2 | 2-CH₃, 6-OCH₃ | oil, NMR δ: 0.85(3H, t)1.20(3H, t) 1.45–2.20(2H, m)3.60(3H, s) 2.77(3H, s)3.30–3.70(4H, m) 6.70–7.52(3H, m)8.73(1H, s) |
| 160 | C₂H₅ | C₂H₅ | 2 | 2,4-(CH₃)₂, 6-OCH₃ | oil, NMR δ: 1.21(6H, t)2.36(3H, d) 2.79(3H, d)3.55(3H, s)3.45(4H, q) 6.50(1H, s)6.60(1H, s)8.68(1H, s) |
| 161 | C₂H₅ | C₂H₅ | 2 | 2,4-(CH₃)₂, 6-OC₃H₇-i | oil, NMR δ: 1.02–1.40(12H, m) 2.37(3H, d)2.78(3H, d)3.53(4H, q) 4.45(1H, m)6.50(1H, s)6.60(1H, s) 8.68(1H, s) |
| 162 | C₂H₅ | C₂H₅ | 2 | 2,6-(OCH₃)₂, 3-CH₃ | oil, NMR δ: 1.19(6H, t)2.20(3H, s) 3.51(4H, q)3.69(3H, s)3.86(3H, s) 6.70(1H, d)7.36(1H, d)8.72(1H, s) |
| 163 | C₂H₅ | C₂H₅ | 2 | 2-COOC₂H₅ | oil, NMR δ: 1.04–1.37(9H, m) 3.45(4H, q)4.25(2H, q) 7.68–7.74(3H, m)8.17–8.40(1H, m) 8.79(1H, s) |
| 164 | C₂H₅ | C₂H₅ | 2 | 2,6-(CH₃)₂, 4-OC₃H₇-i | oil, NMR δ: 1.12–1.35(12H, m)2.65(6H, s) 3.43(4H, q)4.54(1H, m)6.52(2H, s) 8.70(1H, s) |
| 165 | C₂H₅ | n-C₃H₇ | 2 | 2-CH₃, 6-C₂H₅ | oil, NMR δ: 0.73–2.03(11H, m)2.70(3H, s) 2.96–3.70(6H, m)6.96–7.47(3H, m) 8.76(1H, s) |
| 166 | | piperidino | 2 | 2-CH₃, 6-OCH₃ | oil, NMR δ: 1.50–1.98(8H, m)2.73(3H, s) 3.50–3.71(7H, m)6.66–6.88(2H, m) 7.35(1H, s)8.79(1H, s) |
| 167 | C₂H₅ | C₂H₅ | 2 | 2,4,5-(CH₃)₃, 6-OCH₃ | m.p. 138–139° C. |

TABLE 1-continued

| Compound No. | R₁ | R₂ | n | Xm | Physical data |
|---|---|---|---|---|---|
| 168 | $C_2H_5$ | $C_2H_5$ | 2 | 2,3-$CH_2$—$CH_2$—$CH_2$—$CH_2$—**, 6-$OCH_3$ | oil, NMR δ: 1.24(6H, t)1.70-1.91(4H, m) 2.61-2.90(2H, m)3.25-3.69(6H, m) 3.55(3H, s)6.72(1H, d)7.21(1H, d) 8.69(1H, s) |
| 169 | $C_2H_5$ | $C_2H_5$ | 2 | 2,3-$CH_2$—$CH_2$—$CH_2$—****, 6-$OCH_3$. | m.p. 117-118° C. |
| 170 | $C_2H_5$ | $C_2H_5$ | 2 | 3,4-$CH_2$—$CH_2$—$CH_2$—*****, 6-$OCH_3$ | m.p. 151-152° C. |

Note:

*Compound wherein A is 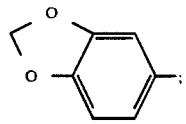

**Compound wherein A is 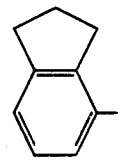

***Compound wherein A is 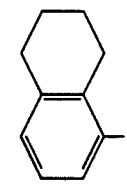

****Compound wherein A is 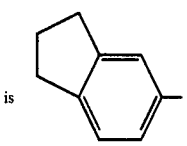

*****Compound wherein A is 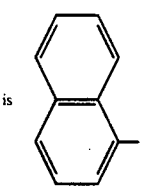

Compounds of the general formula I and mixtures thereof with compounds in the group of known herbicides can be used to weed rice paddies, plowed fields, orchards and non-cultivated land. They can be applied at any time such as prior to sowing the seeds of a crop, simultaneously with sowing, at the time of transplantation, at the seedling stage, or the subsequent growth stage. A suitable method of use can be selected from among various types of treatment including water surface treatment, soil treatment, soil incorporation and foliage treatment.

In order to ensure maximum convenience in handling, compounds of the general formula I and mixtures thereof with compounds in the group of known herbicides may be mixed with various solid or liquid vehicles for common agricultural formulations to prepare various formulations including wettable powders, emulsifiable concentrates oil sprays, dusts, granules and flowables. If desired, various adjuvants may be added to the drug, such as dispersants, diluents, emulsifiers, spreaders, wetting agents, adsorbents, thickeners, antifoams, and antifreezes.

The vehicles to be used may be either solid or liquid or combinations thereof. Illustrative vehicles include: talc, clay, bentonite, kaolin, diatomaceous earth, calcium carbonate, charcoal, starch, gum arabic, water, alcohols, kerosene, naphtha, xylene, cyclohexane, methylnaphthalene, benzene, acetone, dimethylformamide, glycol ether, and N-methylpyrrolidone.

Illustrative adjuvants include: polyoxyethylene alkylphenyl ether, polyoxyethylene sorbitan monooleate, ethylene oxide-propylene oxide copolymer, lignin sulfonates, sorbitan esters, soaps, sulfated oils, alkyl sulfate ester salts, petroleum sulfonates, dioctyl sulfosuccinate salts, alkylbenzene sulfonates, aliphatic amine salts, quaternary ammonium salts, alkyl pyridinium salts, alkyldimethyl betaine, alkylaminoethyl glycine, polyglycol sulfate esters, alkylaminesulfonic acids, isopropyl phosphate, carboxymethyl cellulose, polyvinyl alcohol, hydroxypropyl cellulose, ethylene glycol and xanthan gum.

Compounds of the general formula I can be formulated in amounts freely selected from the range of 0.05-95 wt %. Preferred formulations contain such compounds in amounts of 1-70 wt %, vehicles in amounts of 70-99 wt % (preferably 40-90 wt %), and adjuvants in amounts of 0-20 wt % (preferably 1-7 wt %). Broader activity spectra may be expected if these compounds are used in admixture with other agrichemicals including bactericides, herbicides, growth control regulators, insecticides and acaricides, or with fertilizers.

It will be apparent to those skilled in the art that in the actual use of compounds of the general formula I or admixtures thereof with compounds in the group of known herbicides, the amounts in which they are used should be appropriately selected in accordance with various factors such as the season in which they are used, the weather conditions, method of use, dosage form, place of use, the target weeds and the crop to be treated. As guide figures, 5-500 g, preferably 10-200 g, per are of the compound of the present invention may be used.

The following test examples are given for the purpose of demonstrating the effectiveness of compounds of the present invention as herbicides.

TEST EXAMPLE 1

Wagner pots (1/5,000 are) were filled with the soil (clay loam) from a rice field, which was watered and plowed. The seeds of Echinochloa oryzicola, Monochoria vaginalis, broadleaf weeds (Lindernia pyxidaria, Dopartium junceum, Rotala indica and water starwort) were sown and Scirpus juncoides and the tuber of Cyperus serotimus were bedded on the soil surface. Thereafter, three seedlings (two-leaf stage) of rice plant were planted in each Wagner pot to a depth of 2 cm.

Drugs formulated as granules by the method described in formulation Example 1 (see below) were hand-sprayed in predetermined amounts over the surface of the water at the time when Echinochloa oryzicola germinated. Control and growth were conducted in a greenhouse and the herbicidal effects and extent of crop injury were investigated four weeks after the treatment. The results are summarized in Table 2, in which herbicidal effects and severity of rice plant injury were evaluated on a scale of zero to five by the following criteria:

| Score | Herbicidal effect | Crop injury |
|---|---|---|
| 5 | 100% control (0% weed) | withered and died |
| 4 | 80% control (20% weed) | severe injury |
| 3 | 60% control (40% weed) | medium injury |
| 2 | 40% control (60% weed) | slight injury |
| 1 | 20% control (80% weed) | very slight injury |
| 0 | 0% control (100% weed) | no injury |

For comparison, the following control compounds were used:

Comparison I (see U.S. Pat. No. 4,280,831)

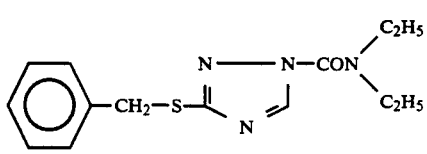

Comparison II (see U.S. Pat. No. 4,280,831)

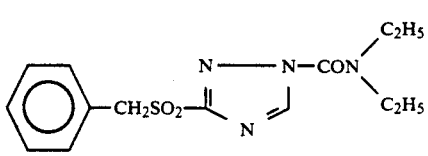

Comparison III (see Japanese Patent Publication for Laying-Open No. 59-39880)

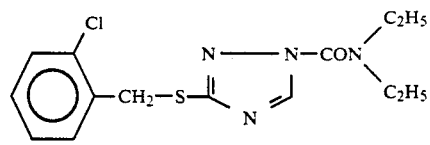

Comparison IV (see Japanese Patent Publication for Laying-Open No. 59-39880)

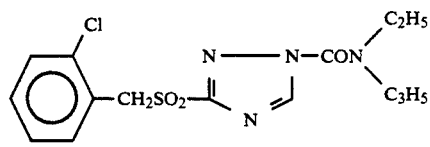

Comparison V (see Japanese Patent Publication for Laying-Open No. 48-77030)

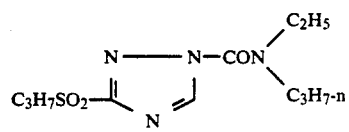

TABLE 2

| | | Herbicidal effect | | | | | |
|---|---|---|---|---|---|---|---|
| Compound No. | Dose (g/a) | Echnochloa oryzicola | Monochoria vaginalis | Broadleaf weeds | Scuroys juncoides | Cyperus serotinus | Crop injury |
| untreated | — | 0 | 0 | 0 | 0 | 0 | 0 |
| 1 | 1.5 | 5 | 5 | 5 | 5 | 2 | 0 |
|  | 3 | 5 | 5 | 5 | 5 | 5 | 0 |
| 2 | 1.5 | 5 | 3 | 3 | 4 | 2 | 0 |
|  | 3 | 5 | 5 | 5 | 5 | 5 | 0 |
| 3 | 0.7 | 5 | 3 | 3 | 5 | 1 | 0 |
|  | 1.5 | 5 | 5 | 4 | 5 | 2 | 0 |
|  | 3 | 5 | 5 | 5 | 5 | 4 | 0 |
| 4 | 0.7 | 5 | 4 | 2 | 5 | 2 | 0 |
|  | 1.5 | 5 | 5 | 4 | 5 | 4 | 0 |
|  | 3 | 5 | 5 | 5 | 5 | 5 | 0 |
|  | 25 | 5 | 5 | 5 | 5 | 5 | 0 |
| 5 | 0.7 | 5 | 2 | 2 | 4 | 2 | 0 |
|  | 1.5 | 5 | 4 | 4 | 5 | 4 | 0 |
|  | 3 | 5 | 5 | 5 | 5 | 5 | 0 |
|  | 25 | 5 | 5 | 5 | 5 | 5 | 0 |
| 6 | 0.7 | 5 | 3 | 5 | 4 | 2 | 0 |
|  | 1.5 | 5 | 5 | 5 | 5 | 4 | 0 |
|  | 3 | 5 | 5 | 5 | 5 | 5 | 0 |
|  | 25 | 5 | 5 | 5 | 5 | 5 | 0 |
| 7 | 0.7 | 5 | 2 | 3 | 4 | 2 | 0 |
|  | 1.5 | 5 | 4 | 4 | 4 | 3 | 0 |
|  | 3 | 5 | 5 | 5 | 5 | 5 | 0 |
|  | 25 | 5 | 5 | 5 | 5 | 5 | 0 |
| 8 | 1.5 | 5 | 4 | 4 | 4 | 2 | 0 |
|  | 3 | 5 | 5 | 5 | 5 | 4 | 0 |
| 9 | 1.5 | 5 | 5 | 1 | 4 | 1 | 0 |
|  | 3 | 5 | 5 | 1 | 4 | 3 | 0 |
| 10 | 0.7 | 5 | 5 | 2 | 5 | 1 | 0 |
|  | 1.5 | 5 | 5 | 5 | 5 | 2 | 0 |
|  | 3 | 5 | 5 | 5 | 5 | 4 | 0 |
| 11 | 1.5 | 5 | 5 | 5 | 5 | 2 | 0 |
|  | 3 | 5 | 5 | 5 | 5 | 3 | 0 |
| 12 | 1.5 | 5 | 5 | 0 | 5 | 2 | 0 |
|  | 3 | 5 | 5 | 5 | 5 | 4 | 0 |
| 13 | 0.7 | 5 | 5 | 5 | 5 | 2 | 0 |
|  | 1.5 | 5 | 5 | 5 | 5 | 4 | 0 |
|  | 3 | 5 | 5 | 5 | 5 | 5 | 0 |
| 14 | 1.5 | 5 | 5 | 3 | 5 | 2 | 0 |

TABLE 2-continued

| Compound No. | Dose (g/a) | Echnochloa oryzicola | Monochoria vaginalis | Broadleaf weeds | Scuroys juncoides | Cyperus serotinus | Crop injury |
|---|---|---|---|---|---|---|---|
| | 3 | 5 | 5 | 4 | 5 | 5 | 0 |
| 15 | 1.5 | 5 | 5 | 4 | 5 | 3 | 0 |
| | 3 | 5 | 5 | 5 | 5 | 5 | 0 |
| 16 | 1.5 | 4 | 2 | 3 | 3 | 1 | 0 |
| | 3 | 5 | 3 | 5 | 5 | 4 | 0 |
| | 25 | 5 | 5 | 5 | 5 | 5 | 0 |
| 20 | 0.7 | 5 | 5 | 5 | 5 | 2 | 0 |
| | 1.5 | 5 | 5 | 5 | 5 | 4 | 0 |
| | 3 | 5 | 5 | 5 | 5 | 5 | 0 |
| | 5 | 5 | 5 | 5 | 5 | 5 | 0 |
| 21 | 1.5 | 4 | 4 | 3 | 3 | 3 | 0 |
| | 3 | 5 | 5 | 5 | 5 | 5 | 0 |
| 23 | 1.5 | 5 | 1 | 0 | 3 | 1 | 0. |
| | 3 | 5 | 5 | 3 | 3 | 3 | 0 |
| 24 | 1.5 | 5 | 5 | 1 | 5 | 2 | 0 |
| | 3 | 5 | 5 | 5 | 5 | 5 | 0 |
| 25 | 1.5 | 4 | 0 | 0 | 4 | 2 | 0 |
| | 3 | 5 | 5 | 5 | 5 | 5 | 0 |
| 26 | 1.5 | 4 | 3 | 2 | 5 | 1 | 0 |
| | 3 | 5 | 3 | 3 | 5 | 3 | 0 |
| 27 | 1.5 | 5 | 5 | 3 | 4 | 3 | 0 |
| | 3 | 5 | 5 | 4 | 4 | 5 | 0 |
| 28 | 1.5 | 5 | 5 | 4 | 3 | 1 | 0 |
| | 3 | 5 | 5 | 4 | 4 | 3 | 0 |
| 29 | 1.5 | 5 | 2 | 0 | 5 | 2 | 0 |
| | 3 | 5 | 5 | 1 | 5 | 4 | 0 |
| 30 | 1.5 | 5 | 0 | 0 | 2 | 2 | 0 |
| | 3 | 5 | 5 | 5 | 2 | 5 | 0 |
| 31 | 1.5 | 5 | 5 | 1 | 5 | 3 | 0 |
| | 3 | 5 | 5 | 5 | 5 | 5 | 0 |
| 32 | 1.5 | 4 | 5 | 2 | 4 | 1 | 0 |
| | 3 | 5 | 5 | 5 | 5 | 3 | 0 |
| 33 | 1.5 | 5 | 4 | 0 | 2 | 2 | 0 |
| | 3 | 5 | 5 | 5 | 5 | 5 | 0 |
| 34 | 1.5 | 5 | 4 | 0 | 3 | 2 | 0 |
| | 3 | 5 | 4 | 0 | 3 | 5 | 0 |
| 35 | 1.5 | 5 | 5 | 4 | 5 | 1 | 0 |
| | 3 | 5 | 5 | 5 | 5 | 4 | 0 |
| 36 | 1.5 | 5 | 2 | 3 | 2 | 1 | 0 |
| | 3 | 5 | 2 | 3 | 5 | 4 | 0 |
| 37 | 1.5 | 5 | 5 | 5 | 5 | 2 | 0 |
| | 3 | 5 | 5 | 5 | 5 | 5 | 0 |
| 38 | 1.5 | 5 | 5 | 5 | 5 | 1 | 0 |
| | 3 | 5 | 5 | 5 | 5 | 4 | 0 |
| 39 | 0.7 | 5 | 4 | 4 | 5 | 1 | 0 |
| | 1.5 | 5 | 5 | 4 | 5 | 2 | 0 |
| | 3 | 5 | 5 | 5 | 5 | 5 | 0 |
| | 25 | 5 | 5 | 5 | 5 | 5 | 0 |
| 40 | 1.5 | 5 | 5 | 1 | 2 | 2 | 0 |
| | 3 | 5 | 5 | 5 | 5 | 4 | 0 |
| 41 | 1.5 | 5 | 5 | 5 | 5 | 1 | 0 |
| | 3 | 5 | 5 | 5 | 5 | 4 | 0 |
| 42 | 1.5 | 5 | 5 | 4 | 5 | 2 | 0 |
| | 3 | 5 | 5 | 5 | 5 | 4 | 0 |
| 43 | 0.7 | 5 | 3 | 1 | 2 | 1 | 0 |
| | 1.5 | 5 | 5 | 2 | 4 | 1 | 0 |
| | 3 | 5 | 5 | 5 | 4 | 3 | 0 |
| 44 | 1.5 | 5 | 5 | 3 | 4 | 1 | 0 |
| | 3 | 5 | 5 | 5 | 5 | 2 | 0 |
| 45 | 1.5 | 5 | 5 | 4 | 5 | 1 | 0 |
| | 3 | 5 | 5 | 5 | 5 | 3 | 0 |
| 46 | 1.5 | 5 | 5 | 5 | 5 | 1 | 0 |
| | 3 | 5 | 5 | 5 | 5 | 3 | 0 |
| 47 | 1.5 | 5 | 5 | 5 | 5 | 2 | 0 |
| | 3 | 5 | 5 | 5 | 5 | 4 | 0 |
| 48 | 1.5 | 5 | 4 | 4 | 4 | 2 | 0 |
| | 3 | 5 | 5 | 4 | 5 | 5 | 0 |
| 49 | 1.5 | 5 | 5 | 4 | 5 | 2 | 0 |
| | 3 | 5 | 5 | 5 | 5 | .5 | 0 |
| 50 | 1.5 | 5 | 4 | 3 | 4 | 2 | 0 |
| | 3 | 5 | 5 | 5 | 5 | 4 | 0 |
| 51 | 1.5 | 4 | 0 | 3 | 3 | 1 | 0 |
| | 3 | 5 | 4 | 4 | 5 | 3 | 0 |
| 52 | 1.5 | 5 | 4 | 4 | 5 | 1 | 0 |
| | 3 | 5 | 5 | 5 | 5 | 4 | 0 |
| 53 | 1.5 | 5 | 5 | 5 | 5 | 2 | 0 |
| 54 | 1.5 | 4 | 5 | 5 | 4 | 1 | 0 |
| | 3 | 5 | 5 | 5 | 4 | 3 | 0 |
| 55 | 1.5 | 5 | 5 | 5 | 3 | 2 | 0 |
| | 3 | 5 | 5 | 5 | 5 | 4 | 0 |
| 56 | 1.5 | 4 | 5 | 5 | 3 | 1 | 0 |
| | 3 | 5 | 5 | 5 | 5 | 3 | 0 |
| 61 | 0.7 | 4 | 5 | 5 | 5 | 2 | 0 |
| | 1.5 | 5 | 5 | 5 | 5 | 4 | 0 |
| | 3 | 5 | 5 | 5 | 5 | 5 | 0 |
| 62 | 0.7 | 5 | 1 | 2 | 3 | 2 | 0 |
| | 1.5 | 5 | 5 | 5 | 5 | 4 | 0 |
| | 3 | 5 | 5 | 5 | 5 | 5 | 0 |
| 63 | 0.7 | 1 | 1 | 2 | 1 | 2 | 0 |
| | 1.5 | 4 | 3 | 4 | 3 | 3 | 0 |
| | 3 | 5 | 5 | 5 | 5 | 5 | 0 |
| 64 | 0.7 | 5 | 2 | 2 | 2 | 2 | 0 |
| | 1.5 | 5 | 5 | 4 | 5 | 4 | 0 |
| | 3 | 5 | 5 | 5 | 5 | 5 | 0 |
| 65 | 1.5 | 4 | 0 | 1 | 0 | 0 | 0 |
| | 3 | 5 | 0 | 3 | 1 | 0 | 0 |
| 67 | 1.5 | 5 | 1 | 1 | 1 | 3 | 0 |
| | 3 | 5 | 2 | 3 | 3 | 4 | 0 |
| 71 | 1.5 | 5 | 2 | 2 | 4 | 3 | 0 |
| | 3 | 5 | 3 | 4 | 5 | 5 | 0 |
| 74 | 1.5 | 5 | 3 | 4 | 5 | 4 | 0 |
| | 3 | 5 | 5 | 5 | 5 | 5 | 0 |
| 78 | 1.5 | 5 | 5 | 5 | 5 | 4 | 0 |
| | 3 | 5 | 5 | 5 | 5 | 5 | 0 |
| 79 | 0.7 | 5 | 4 | 4 | 4 | 1 | 0 |
| | 1.5 | 5 | 5 | 5 | 5 | 3 | 0 |
| | 3 | 5 | 5 | 5 | 5 | 5 | 0 |
| | 25 | 5 | 5 | 5 | 5 | 5 | 0 |
| 80 | 1.5 | 5 | 2 | 2 | 1 | 3 | 0 |
| | 3 | 5 | 3 | 4 | 3 | 5 | 0 |
| 81 | 1.5 | 5 | 5 | 1 | 5 | 2 | 0 |
| | 3 | 5 | 5 | 4 | 5 | 5 | 0 |
| 82 | 1.5 | 5 | 5 | 1 | 3 | 2 | 0 |
| | 3 | 5 | 5 | 3 | 5 | 5 | 0 |
| 83 | 1.5 | 4 | 0 | 0 | 0 | 1 | 0 |
| | 3 | 5 | 5 | 4 | 5 | 3 | 0 |
| 84 | 1.5 | 5 | 5 | 3 | 5 | 2 | 0 |
| | 3 | 5 | 5 | 5 | 5 | 5 | 0 |
| 85 | 1.5 | 5 | 3 | 4 | 2 | 2 | 0 |
| | 3 | 5 | 5 | 5 | 4 | 4 | 0 |
| 86 | 1.5 | 5 | 5 | 4 | 5 | 2 | 0 |
| | 3 | 5 | 5 | 5 | 5 | 4 | 0 |
| 87 | 1.5 | 5 | 5 | 4 | 5 | 1 | 0 |
| | 3 | 5 | 5 | 5 | 5 | 4 | 0 |
| 88 | 0.7 | 5 | 3 | 3 | 2 | 2 | 0 |
| | 1.5 | 5 | 5 | 5 | 5 | 4 | 0 |
| | 3 | 5 | 5 | 5 | 5 | 5 | 0 |
| 89 | 1.5 | 4 | 0 | 4 | 0 | 0 | 0 |
| | 3 | 5 | 0 | 5 | 0 | 0 | 0 |
| 93 | 1.5 | 4 | 0 | 0 | 0 | 0 | 0 |
| | 3 | 5 | 0 | 0 | 0 | 0 | 0 |
| 94 | 1.5 | 5 | 2 | 4 | 0 | 2 | 0 |
| | 3 | 5 | 4 | 5 | 1 | 4 | 0 |
| 100 | 1.5 | 5 | 4 | 4 | 3 | 1 | 0 |
| | 3 | 5 | 4 | 4 | 4 | 4 | 0 |
| 101 | 0.7 | 5 | 1 | 3 | 1 | 2 | 0 |
| | 1.5 | 5 | 5 | 4 | 3 | 3 | 0 |
| | 3 | 5 | 5 | 5 | 5 | 5 | 0 |
| | 25 | 5 | 5 | 5 | 5 | 5 | 0 |
| 102 | 1.5 | 5 | 2 | 3 | 1 | 1 | 0 |
| | 3 | 5 | 4 | 5 | 3 | 5 | 0 |
| 106 | 1.5 | 4 | 1 | 1 | 1 | 1 | 0 |
| | 3 | 5 | 3 | 4 | 2 | 3 | 0 |
| 110 | 1.5 | 5 | 2 | 3 | 2 | 2 | 0 |
| | 3 | 5 | 4 | 4 | 3 | 4 | 0 |
| 111 | 1.5 | 5 | 2 | 5 | 2 | 1 | 0 |
| | 3 | 5 | 3 | 5 | 3 | 4 | 0 |
| 122 | 1.5 | 5 | 5 | 5 | 5 | 2 | 0 |
| | 3 | 5 | 5 | 5 | 5 | 4 | 0 |
| 126 | 1.5 | 4 | 5 | 4 | 2 | 1 | 0 |
| | 3 | 5 | 5 | 5 | 5 | 3 | 0 |

TABLE 2-continued

| Compound No. | Dose (g/a) | Echnochloa oryzicola | Monochoria vaginalis | Broad-leaf weeds | Scuroys juncoides | Cyperus serotinus | Crop injury |
|---|---|---|---|---|---|---|---|
| 127 | 1.5 | 5 | 5 | 3 | 4 | 2 | 0 |
|  | 3 | 5 | 5 | 5 | 4 | 4 | 0 |
| 128 | 1.5 | 5 | 5 | 5 | 5 | 1 | 0 |
|  | 3 | 5 | 5 | 5 | 5 | 4 | 0 |
| 129 | 1.5 | 4 | 5 | 4 | 2 | 1 | 0 |
|  | 3 | 5 | 5 | 5 | 2 | 3 | 0 |
| 133 | 1.5 | 5 | 3 | 3 | 4 | 0 | 0 |
|  | 3 | 5 | 4 | 4 | 4 | 4 | 0 |
| 137 | 1.5 | 4 | 2 | 3 | 2 | 1 | 0 |
|  | 3 | 5 | 5 | 4 | 4 | 4 | 0 |
| 138 | 1.5 | 5 | 5 | 3 | 2 | 1 | 0 |
|  | 3 | 5 | 5 | 4 | 3 | 3 | 0 |
| 141 | 1.5 | 4 | 2 | 0 | 0 | 2 | 0 |
|  | 3 | 5 | 5 | 1 | 1 | 3 | 0 |
| 142 | 1.5 | 5 | 5 | 1 | 5 | 2 | 0 |
|  | 3 | 5 | 5 | 5 | 5 | 4 | 2 |
| 143 | 1.5 | 4 | 2 | 4 | 4 | 3 | 0 |
|  | 3 | 5 | 5 | 5 | 5 | 4 | 0 |
| 147 | 1.5 | 5 | 2 | 2 | 0 | 1 | 0 |
|  | 3 | 5 | 3 | 3 | 1 | 4 | 0 |
| 151 | 1.5 | 5 | 3 | 5 | 4 | 2 | 0 |
|  | 3 | 5 | 5 | 5 | 4 | 4 | 0 |
| 154 | 1.5 | 5 | 5 | 0 | 3 | 2 | 0 |
|  | 3 | 5 | 5 | 4 | 4 | 4 | 0 |
| 155 | 1.5 | 5 | 5 | 1 | 5 | 2 | 0 |
|  | 3 | 5 | 5 | 4 | 5 | 4 | 0 |
| 156 | 1.5 | 5 | 4 | 1 | 5 | 2 | 0 |
|  | 3 | 5 | 5 | 4 | 5 | 3 | 0 |
| 157 | 1.5 | 5 | 5 | 5 | 5 | 2 | 0 |
|  | 3 | 5 | 5 | 5 | 5 | 4 | 0 |
| 158 | 1.5 | 5 | 5 | 5 | 5 | 2 | 0 |
|  | 3 | 5 | 5 | 5 | 5 | 4 | 0 |
| 159 | 1.5 | 5 | 5 | 3 | 5 | 2 | 0 |
|  | 3 | 5 | 5 | 5 | 5 | 4 | 0 |
| 160 | 1.5 | 5 | 5 | 3 | 5 | 2 | 0 |
|  | 3 | 5 | 5 | 5 | 5 | 4 | 0 |
| 161 | 1.5 | 5 | 5 | 3 | 5 | 3 | 0 |
|  | 3 | 5 | 5 | 4 | 5 | 4 | 0 |
| 162 | 1.5 | 5 | 0 | 1 | 4 | 1 | 0 |
|  | 3 | 5 | 3 | 2 | 5 | 3 | 0 |
| 163 | 1.5 | 5 | 0 | 0 | 4 | 1 | 0 |
|  | 3 | 5 | 4 | 2 | 5 | 3 | 0 |
| 164 | 1.5 | 5 | 3 | 3 | 5 | 2 | 0 |
|  | 3 | 5 | 5 | 5 | 5 | 4 | 0 |
| 165 | 1.5 | 5 | 4 | 3 | 5 | 2 | 0 |
|  | 3 | 5 | 5 | 5 | 5 | 4 | 0 |
| 166 | 1.5 | 5 | 3 | 2 | 3 | 1 | 0 |
|  | 3 | 5 | 4 | 4 | 3 | 3 | 0 |
| 167 | 1.5 | 5 | 5 | 3 | 5 | 2 | 0 |
|  | 3 | 5 | 5 | 5 | 5 | 4 | 0 |
| 168 | 1.5 | 5 | 2 | 0 | 0 | 1 | 0 |
|  | 3 | 5 | 4 | 3 | 4 | 3 | 0 |
| 169 | 1.5 | 5 | 3 | 2 | 4 | 1 | 0 |
|  | 3 | 5 | 5 | 5 | 5 | 3 | 0 |
| 170 | 1.5 | 5 | 2 | 0 | 5 | 2 | 0 |
|  | 3 | 5 | 5 | 4 | 5 | 3 | 0 |
| Comparison I | 0.7 | 0 | 0 | 0 | 0 | 0 | 0 |
|  | 1.5 | 0 | 0 | 0 | 0 | 0 | 0 |
|  | 3 | 1 | 1 | 0 | 0 | 2 | 0 |
|  | 6 | 2 | 1 | 1 | 1 | 3 | 0 |
|  | 12.5 | 4 | 2 | 2 | 2 | 4 | 1 |
|  | 25 | 5 | 3 | 3 | 3 | 5 | 2 |
| Comparison III | 0.7 | 1 | 0 | 0 | 0 | 1 | 0 |
|  | 1.5 | 2 | 1 | 0 | 1 | 2 | 0 |
|  | 3 | 5 | 3 | 1 | 3 | 3 | 0 |
|  | 6 | 5 | 4 | 3 | 4 | 4 | 3 |
|  | 12.5 | 5 | 4 | 5 | 5 | 5 | 3 |
|  | 25 | 5 | 5 | 5 | 5 | 5 | 4 |
| Comparison IV | 0.7 | 0 | 0 | 0 | 0 | 0 | 0 |
|  | 1.5 | 0 | 0 | 0 | 0 | 1 | 0 |
|  | 3 | 1 | 0 | 0 | 0 | 1 | 0 |
|  | 6 | 2 | 2 | 1 | 2 | 2 | 0 |
|  | 12.5 | 5 | 3 | 3 | 2 | 2 | 0 |
|  | 25 | 5 | 4 | 4 | 3 | 4 | 0 |
| Comparison V | 0.7 | 1 | 0 | 0 | 0 | 1 | 0 |
|  | 1.5 | 2 | 0 | 0 | 1 | 2 | 0 |
|  | 3 | 4 | 1 | 1 | 2 | 3 | 0 |
|  | 6 | 5 | 2 | 3 | 4 | 4 | 0 |
|  | 12.5 | 5 | 4 | 5 | 4 | 5 | 1 |
|  | 25 | 5 | 5 | 5 | 5 | 5 | 0 |
| Comparison V | 0.7 | 4 | 0 | 1 | 0 | 1 | 1 |
|  | 1.5 | 5 | 1 | 1 | 1 | 3 | 1 |
|  | 3 | 5 | 2 | 2 | 3 | 3 | 2 |
|  | 6 | 5 | 3 | 3 | 4 | 3 | 3 |
|  | 12.5 | 5 | 4 | 5 | 4 | 5 | 3 |
|  | 25 | 5 | 5 | 5 | 5 | 5 | 4 |

TEST EXAMPLE 2

Wagner pots (1/5,000 are) were filled with the soil (clay loam) from a rice field, which was watered and plowed. The seeds of Echinochloa oryzicola, Monochoria vaginalis, and broad-leaf weeds (Lindernia pyxidaria, Dopartium junceum, Rotala indica and water starwort) were sown, and three seedlings (two-leaf stage) of rice plant were planted in each Wagner pot to a depth of 2 cm. Drugs formulated as wettable powders by the method described in Formulation Example 2 (see below) were weighed, diluted in 5 ml of water per pot and sprinkled over the surface of the water at the time when Echinochloa oryzicola was at the 2- to 2.5-leaf stage. Control and growth were conducted in a green-house and the herbicidal effects and degree of crop injury were investigated four weeks after the treatment. The results are summarized in Table 3, in which the individual scores have the same meanings as defined in Test Example 1. The five control compounds were also the same as those employed in Test Example 1.

TABLE 3

| Compound No. | Dose (g/a) | Echinola orycola | Monochoria vaginalis | Broadleaf weeds | Crop injury |
|---|---|---|---|---|---|
| untreated | — | 0 | 0 | 0 | 0 |
| 2 | 1.5 | 5 | 2 | 2 | 0 |
|  | 3 | 5 | 3 | 2 | 0 |
|  | 6 | 5 | 3 | 4 | 0 |
| 3 | 1.5 | 5 | 1 | 2 | 0 |
|  | 3 | 5 | 2 | 2 | 0 |
|  | 6 | 5 | 5 | 4 | 0 |
| 4 | 1.5 | 5 | 2 | 1 | 0 |
|  | 3 | 5 | 3 | 2 | 0 |
|  | 6 | 5 | 3 | 3 | 0 |
|  | 12.5 | 5 | 5 | 4 | 0 |
|  | 25 | 5 | 5 | 5 | 0 |
| 5 | 1.5 | 5 | 2 | 1 | 0 |
|  | 3 | 5 | 2 | 2 | 0 |
|  | 6 | 5 | 3 | 4 | 0 |
|  | 12.5 | 5 | 4 | 4 | 0 |
|  | 25 | 5 | 5 | 5 | 0 |
| 6 | 1.5 | 5 | 2 | 2 | 0 |
|  | 3 | 5 | 3 | 2 | 0 |
|  | 6 | 5 | 3 | 3 | 0 |
|  | 12.5 | 5 | 4 | 3 | 0 |
|  | 25 | 5 | 5 | 5 | 0 |
| 7 | 1.5 | 5 | 2 | 1 | 0 |
|  | 3 | 5 | 2 | 2 | 0 |
|  | 6 | 5 | 4 | 3 | 0 |
|  | 12.5 | 5 | 4 | 3 | 0 |
|  | 25 | 5 | 5 | 4 | 0 |
| 8 | 1.5 | 5 | 1 | 0 | 0 |
|  | 3 | 5 | 3 | 1 | 0 |
|  | 6 | 5 | 5 | 4 | 0 |
| 9 | 1.5 | 5 | 3 | 1 | 0 |
|  | 3 | 5 | 3 | 2 | 0 |

TABLE 3-continued

| Compound No. | Dose (g/a) | Echinola orycola | Monochoria vaginalis | Broadleaf weeds | Crop injury |
|---|---|---|---|---|---|
| | 6 | 5 | 3 | 2 | 0 |
| 10 | 1.5 | 5 | 1 | 1 | 0 |
| | 3 | 5 | 2 | 2 | 0 |
| | 6 | 5 | 5 | 4 | 0 |
| 11 | 3 | 5 | 3 | 1 | 0 |
| | 6 | 5 | 3 | 3 | 0 |
| 13 | 1.5 | 5 | 3 | 1 | 0 |
| | 3 | 5 | 3 | 2 | 0 |
| | 6 | 5 | 3 | 2 | 0 |
| 14 | 3 | 5 | 3 | 3 | 0 |
| | 6 | 5 | 4 | 3 | 0 |
| 15 | 1.5 | 5 | 1 | 0 | 0 |
| | 3 | 5 | 2 | 1 | 0 |
| 16 | 1.5 | 5 | 1 | 2 | 0 |
| | 3 | 5 | 2 | 2 | 0 |
| | 6 | 5 | 3 | 3 | 0 |
| | 12.5 | 5 | 3 | 5 | 0 |
| | 25 | 5 | 5 | 5 | 0 |
| 20 | 1.5 | 4 | 3 | 1 | 0 |
| | 3 | 5 | 3 | 2 | 0 |
| | 6 | 5 | 3 | 2 | 0 |
| | 12.5 | 5 | 3 | 4 | 0 |
| | 25 | 5 | 5 | 5 | 0 |
| 21 | 3 | 4 | 1 | 2 | 0 |
| | 6 | 5 | 2 | 4 | 0 |
| 24 | 3 | 5 | 2 | 3 | 0 |
| | 6 | 5 | 4 | 4 | 0 |
| 25 | 3 | 5 | 2 | 1 | 0 |
| | 6 | 5 | 3 | 2 | 0 |
| 26 | 3 | 3 | 2 | 1 | 0 |
| | 6 | 5 | 2 | 3 | 0 |
| 27 | 3 | 5 | 2 | 2 | 0 |
| | 6 | 5 | 3 | 4 | 0 |
| 28 | 3 | 4 | 3 | 2 | 0 |
| | 6 | 5 | 3 | 3 | 0 |
| 39 | 1.5 | 5 | 1 | 2 | 0 |
| | 3 | 5 | 1 | 3 | 0 |
| | 6 | 5 | 2 | 3 | 0 |
| | 12.5 | 5 | 4 | 4 | 0 |
| | 25 | 5 | 5 | 4 | 0 |
| 47 | 3 | 5 | 2 | 4 | 0 |
| | 6 | 5 | 4 | 4 | 0 |
| 49 | 3 | 5 | 2 | 3 | 0 |
| | 6 | 5 | 3 | 3 | 0 |
| 51 | 3 | 4 | 2 | 1 | 0 |
| | 6 | 5 | 3 | 2 | 0 |
| 52 | 3 | 5 | 3 | 2 | 0 |
| | 6 | 5 | 3 | 4 | 0 |
| 53 | 3 | 5 | 2 | 2 | 0 |
| | 6 | 5 | 3 | 4 | 0 |
| 54 | 3 | 5 | 2 | 2 | 0 |
| | 6 | 5 | 2 | 3 | 0 |
| 61 | 1.5 | 5 | 3 | 1 | 0 |
| | 3 | 5 | 3 | 2 | 0 |
| | 6 | 5 | 3 | 2 | 0 |
| 74 | 3 | 5 | 2 | 1 | 0 |
| | 6 | 5 | 3 | 3 | 0 |
| 78 | 3 | 5 | 2 | 2 | 0 |
| | 6 | 5 | 3 | 3 | 0 |
| 79 | 3 | 5 | 3 | 3 | 0 |
| | 6 | 5 | 3 | 3 | 0 |
| 80 | 3 | 4 | 1 | 3 | 0 |
| | 6 | 5 | 3 | 4 | 0 |
| 81 | 3 | 5 | 3 | 3 | 0 |
| | 6 | 5 | 3 | 3 | 0 |

TABLE 3-continued

| Compound No. | Dose (g/a) | Echinola orycola | Monochoria vaginalis | Broadleaf weeds | Crop injury |
|---|---|---|---|---|---|
| 82 | 3 | 5 | 1 | 3 | 0 |
| | 6 | 5 | 4 | 3 | 0 |
| 83 | 3 | 4 | 0 | 0 | 0 |
| | 6 | 5 | 1 | 2 | 0 |
| 84 | 3 | 5 | 2 | 1 | 0 |
| | 6 | 5 | 3 | 1 | 0 |
| 86 | 3 | 5 | 2 | 2 | 0 |
| | 6 | 5 | 3 | 2 | 0 |
| 88 | 1.5 | 5 | 0 | 0 | 0 |
| | 3 | 5 | 2 | 1 | 0 |
| | 6 | 5 | 4 | 3 | 0 |
| 94 | 3 | 5 | 1 | 2 | 0 |
| | 6 | 5 | 4 | 3 | 0 |
| 100 | 3 | 4 | 0 | 3 | 0 |
| | 6 | 5 | 1 | 3 | 0 |
| 101 | 3 | 5 | 1 | 3 | 0 |
| | 6 | 5 | 2 | 4 | 0 |
| 102 | 3 | 4 | 1 | 3 | 0 |
| | 6 | 5 | 2 | 3 | 0 |
| Comparison I | 1.5 | 0 | 0 | 0 | 0 |
| | 3 | 0 | 0 | 0 | 0 |
| | 6 | 0 | 0 | 0 | 0 |
| | 12.5 | 1 | 0 | 0 | 0 |
| | 25 | 2 | 1 | 2 | 1 |
| Comparison II | 1.5 | 0 | 0 | 0 | 0 |
| | 3 | 1 | 0 | 0 | 0 |
| | 6 | 3 | 0 | 0 | 0 |
| | 12.5 | 4 | 1 | 1 | 1 |
| | 25 | 5 | 3 | 3 | 2 |
| Comparison III | 1.5 | 0 | 0 | 0 | 0 |
| | 3 | 0 | 0 | 0 | 0 |
| | 6 | 0 | 0 | 0 | 0 |
| | 12.5 | 0 | 0 | 0 | 0 |
| | 25 | 1 | 0 | 0 | 1 |
| Comparison IV | 1.5 | 0 | 0 | 0 | 0 |
| | 3 | 1 | 0 | 0 | 0 |
| | 6 | 3 | 0 | 0 | 0 |
| | 12.5 | 4 | 0 | 1 | 0 |
| | 25 | 5 | 3 | 3 | 1 |
| Comparison V | 1.5 | 1 | 0 | 0 | 0 |
| | 3 | 3 | 0 | 0 | 0 |
| | 6 | 4 | 1 | 1 | 1 |
| | 12.5 | 5 | 2 | 2 | 2 |
| | 25 | 5 | 3 | 4 | 3 |

TEST EXAMPLE 3

Wagner pots (1/5,000 area) were filled with the soil (clay loam) from a plowed field. After sowing wheat and soybean seeds, they were covered with the soil from a plowed field containing weed seeds. The soil covering had a thickness of 2 cm. Immediately thereafter, emulsifiable concentrates formulated by the method described in Formulation Example 3 (see below) were weighed, diluted in 5 ml of water per pot and sprinkled over the soil surface. Control and growth were conducted in a greenhouse and the herbicidal effects and extent of crop injury were investigated four weeks after the treatment. The results are summarized in Table 4, in which the individual scores have the same meanings as defined in Test Example 1.

TABLE 4

| Compound No. | Dose (g/a) | Amaranthus ascendens | Digitaria adscendens | Amaranthus retroflexus | Persicaria nodosa | Crop injury Wheat | Crop injury Soybean |
|---|---|---|---|---|---|---|---|
| untreated | — | 0 | 0 | 0 | 0 | 0 | 0 |
| 2 | 5 | 4 | 5 | 3 | 4 | 0 | 0 |
| 2 | 10 | 5 | 5 | 4 | 5 | 0 | 0 |
| 4 | 5 | 5 | 5 | 3 | 2 | 0 | 0 |
| 4 | 10 | 5 | 5 | 4 | 4 | 0 | 0 |
| 5 | 5 | 5 | 5 | 2 | 3 | 0 | 0 |
| 5 | 10 | 5 | 5 | 3 | 3 | 0 | 0 |

TABLE 4-continued

| Compound No. | Dose (g/a) | Herbicidal effect | | | | Crop injury | |
|---|---|---|---|---|---|---|---|
| | | *Amaranthus ascendens* | *Digitaria adscendens* | *Amaranthus retroflexus* | *Persicaria nodosa* | Wheat | Soybean |
| 6 | 5 | 5 | 5 | 2 | 3 | 0 | 0 |
| 6 | 10 | 5 | 5 | 4 | 4 | 0 | 0 |
| 7 | 5 | 5 | 5 | 3 | 4 | 0 | 0 |
| 7 | 10 | 5 | 5 | 4 | 4 | 0 | 0 |
| 14 | 5 | 5 | 5 | 2 | 2 | 0 | 0 |
| 14 | 10 | 5 | 5 | 3 | 4 | 0 | 0 |
| 15 | 5 | 5 | 5 | 4 | 3 | 0 | 0 |
| 15 | 10 | 5 | 5 | 4 | 4 | 0 | 0 |
| 16 | 5 | 5 | 5 | 2 | 3 | 0 | 0 |
| 16 | 10 | 5 | 5 | 3 | 3 | 0 | 0 |
| 20 | 5 | 5 | 5 | 4 | 4 | 0 | 0 |
| 24 | 5 | 5 | 5 | 1 | 2 | 0 | 0 |
| 24 | 10 | 5 | 5 | 3 | 2 | 0 | 0 |
| 39 | 5 | 5 | 5 | 3 | 2 | 0 | 0 |
| 39 | 10 | 5 | 5 | 3 | 4 | 0 | 0 |
| 67 | 5 | 3 | 4 | 2 | 2 | 0 | 0 |
| 67 | 10 | 5 | 5 | 3 | 0 | 0 | 0 |
| 74 | 5 | 4 | 4 | 3 | 3 | 0 | 0 |
| 74 | 10 | 5 | 5 | 5 | 4 | 0 | 0 |
| 106 | 5 | 3 | 4 | 2 | 2 | 0 | 0 |
| 106 | 10 | 5 | 5 | 3 | 3 | 0 | 0 |
| 133 | 5 | 5 | 5 | 3 | 3 | 0 | 0 |
| 133 | 10 | 5 | 5 | 4 | 4 | 0 | 0 |
| 143 | 5 | 4 | 4 | 2 | 3 | 0 | 0 |
| 143 | 10 | 5 | 5 | 4 | 3 | 0 | 0 |

TEST EXAMPLE 4

Wagner pots (1/5,000 are) were filled with the soil (clay loam) from a rice field, which was watered and plowed. The seeds of *Echinochloa oryzicola*, broadleaf weeds (*Lindernia pyxidaria, Dopartium junceum, Rotala indica* and water starwort) and *Scirpus juncoides*, and the tubers of *Cyperus serotinus* and *Sagittaria pygmaea* were planted in the plowed soil. Thereafter, three seedlings (two-leaf stage) of rice plant were planted in each Wagner pot to a depth of 2 cm.

Seven days after the seeding of weeds (i.e. at the time when *Echinochloa oryzicola* was at the one-leaf stage), granules formulated by the method described in Formulation Example 4 were hand-sprayed in predetermined amounts over the surface of the water. Control and growth were conducted in a greenhouse and the herbicidal effects and extent of crop injury were investigated three weeks after the treatment. The results are summarized in Table 5, in which herbicidal effects and severity of rice plant injury were evaluated on a scale of zero to five by the following criteria:

| Score | Herbicidal effect | Crop injury |
|---|---|---|
| 5 | ≧90% control (withered almost completely) | withered and death |
| 4 | 70–89% control | severe injury |
| 3 | 40–69% control | medium injury |
| 2 | 20–39% control | Slight injury |
| 1 | 6–19% control | very slight injury |
| 0 | ≦5% control (practically ineffective) | no injury |

The parenthesized figures in Table 5 represent the "expected" responses (e) of herbicide combinations in weed control that were calculated by the following Colby equations (Colby, S. R., WEEDS, 15, 20–22, 1967):

i) Combination of two herbicides:

$$E = \alpha + \frac{\beta(5 - \alpha)}{5}$$

$\alpha, \beta$: the percent control values of weed growth accomplished by the herbicide components when applied individually;

$$E = \alpha + \beta + \gamma - \frac{\alpha\beta + \beta\gamma + \gamma\alpha}{5} + \frac{\alpha\beta\gamma}{5 \times 5}$$

$\alpha, \beta, \gamma$: the percent control values of weed growth attained by the herbicide components when applied individually.

TABLE 5

| Compound No. | Dose (g/a) | Herbicidal effect | | | | | Crop injury |
|---|---|---|---|---|---|---|---|
| | | *Echinochloa oryzicola* | Broadleaf weeds | *Scirpus juncoides* | *Cyperus serotinus* | *Sagittaria pygmaea* | |
| Compound No. 6 | 0.5 | 2 | 1 | 1 | 2 | 0 | 0 |
| | 1 | 3 | 1 | 2 | 2 | 0 | 0 |
| | 2 | 5 | 3 | 3 | 4 | 0 | 0 |
| Compound No. 4 | 0.5 | 2 | 1 | 1 | 2 | 0 | 0 |
| | 1 | 3 | 1 | 2 | 2 | 0 | 0 |
| | 2 | 5 | 3. | 2 | 4 | 0 | 0 |
| Compound No. 1 | 0.5 | 3 | 0 | 0 | 2 | 0 | 0 |
| | 1 | 3 | 1 | 1 | 2 | 0 | 0 |
| | 2 | 5 | 2 | 2 | 3 | 0 | 0 |
| Compound | 0.5 | 2 | 0 | 0 | 2 | 0 | 0 |

TABLE 5-continued

| Compound No. | Dose (g/a) | Herbicidal effect | | | | | Crop injury |
|---|---|---|---|---|---|---|---|
| | | Echinochloa oryzicola | Broadleaf weeds | Scirpus juncoides | Cyperus serotinus | Sagittaria pygmaea | |
| No. 10 | 1 | 3 | 1 | 1 | 2 | 0 | 0 |
| | 2 | 5 | 3 | 2 | 4 | 0 | 0 |
| Pyrazolate | 5 | 3 | 3 | 2 | 1 | 3 | 0 |
| | 10 | 3 | 4 | 3 | 2 | 4 | 0 |
| Pyrazoxyfen | 5 | 3 | 3 | 2 | 1 | 3 | 0 |
| | 10 | 3 | 4 | 3 | 2 | 4 | 0 |
| Bensofenap | 5 | 2 | 3 | 2 | 1 | 3 | 0 |
| | 10 | 3 | 4 | 3 | 2 | 4 | 0 |
| Bromobutide | 0.5 | 0 | 0 | 3 | 1 | 0 | 0 |
| | 1 | 1 | 0 | 4 | 2 | 1 | 0 |
| Clomeprop | 1 | 0 | 2 | 2 | 1 | 2 | 0 |
| | 2 | 0 | 4 | 4 | 2 | 4 | 0 |
| Bensulfuron methyl | 0.1 | 1 | 5 | 4 | 4 | 4 | 0 |
| | 0.5 | 3 | 5 | 5 | 5 | 4 | 2 |
| Pyrazosulfuron ethyl | 0.1 | 3 | 5 | 5 | 5 | 4 | 0 |
| | 0.5 | 4 | 5 | 5 | 5 | 5 | 3 |
| CG-148 | 0.1 | 1 | 5 | 4 | 4 | 4 | 0 |
| | 0.5 | 3 | 5 | 5 | 5 | 5 | 3 |
| Compound No. 6 + | 0.5 + 5 | 4 (3.8) | 5 (3.4) | 4 (2.6) | 4 (2.6) | 4 (3.0) | 0 |
| Pyrazolate | 1 + 10 | 5 (4.2) | 5 (4.2) | 5 (3.8) | 5 (3.2) | 5 (3.0) | 0 |
| Compound No. 6 + | 0.5 + 5 | 4 (3.8) | 5 (3.4) | 4 (2.6) | 4 (2.6) | 4 (3.0) | 0 |
| Pyrazoxyfen | 1 + 5 | 5 (4.2) | 5 (3.4) | 5 (3.2) | 5 (2.6) | 5 (3.0) | 0 |
| Compound No. 6 + | 0.5 + 5 | 4 (3.2) | 5 (3.4) | 4 (2.6) | 4 (2.6) | 4 (3.0) | 0 |
| Bensofenap | 1 + 10 | 5 (4.2) | 5 (4.2) | 5 (3.8) | 5 (3.2) | 5 (4.0) | 0 |
| Compound No. 4 + | 0.5 + 5 | 4 (3.8) | 5 (3.4) | 4 (2.6) | 4 (2.6) | 4 (3.0) | 0 |
| Pyrazolate | 1 + 10 | 5 (4.2) | 5 (4.2) | 5 (3.8) | 5 (3.2) | 5 (4.0) | 0 |
| Compound No. 4 + | 0.5 + 10 | 5 (3.8) | 5 (4.2) | 4 (3.4) | 4 (3.2) | 5 (4.0) | 0 |
| Pyrazoxyfen | 1 + 10 | 5 (4.2) | 5 (4.2) | 5 (3.8) | 5 (3.2) | 5 (4.0) | 0 |
| Compound No. 4 + | 0.5 + 5 | 4 (3.2) | 5 (3.4) | 4 (2.6) | 4 (2.6) | 4 (3.0) | 0 |
| Bensofenap | 1 + 10 | 5 (4.2) | 5 (4.2) | 5 (3.8) | 5 (3.2) | 5 (4.0) | 0 |
| Compound No. 1 + | 0.5 + 10 | 5 (4.2) | 5 (4.0) | 4 (3.0) | 4 (3.2) | 5 (4.0) | 0 |
| Pyrazolate | 1 + 10 | 5 (4.2) | 5 (4.2) | 5 (3.4) | 5 (3.2) | 5 (4.0) | 0 |
| Compound No. 1 + | 0.5 + 5 | 4 (4.2) | 4 (3.0) | 4 (2.0) | 4 (2.6) | 4 (3.0) | 0 |
| Pyrazoxyfen | 1 + 10 | 5 (4.2) | 5 (4.2) | 5 (3.4) | 5 (3.2) | 5 (4.0) | 0 |
| Compound No. 1 + | 1 + 5 | 5 (3.8) | 5 (3.4) | 5 (2.6) | 5 (2.6) | 5 (3.0) | 0 |
| Bensofanap | 1 + 10 | 5 (4.2) | 5 (4.2) | 5 (3.4) | 5 (3.2) | 5 (4.0) | 0 |
| Compound No. 10 + | 0.5 + 5 | 4 (3.8) | 4 (3.0) | 4 (2.0) | 4 (2.6) | 4 (3.0) | 0 |
| Pyrazolate | 1 + 10 | 5 (4.2) | 5 (4.2) | 5 (3.4) | 5 (3.2) | 5 (4.0) | 0 |
| Compound No. 10 + | 0.5 + 5 | 4 (3.8) | 4 (3.0) | 4 (2.0) | 4 (2.6) | 4 (3.0) | 0 |
| Pyrazoxyfen | 1 + 10 | 5 (3.8) | 5 (4.0) | 4 (3.0) | 4 (3.2) | 5 (4.0) | 0 |
| Compound No. 10 + | 0.5 + 5 | 4 (3.2) | 4 (3.0) | 4 (2.0) | 4 (2.6) | 4 (3.0) | 0 |
| Bensofanap | 1 + 10 | 5 (4.2) | 5 (4.2) | 5 (3.4) | 5 (3.2) | 5 (4.0) | 0 |
| Compound No. 6 + | 0.5 + 5 + 0.5 | 5 (3.80) | 5 (3.40) | 5 (4.04) | 5 (3.08) | 5 (3.00) | 0 |
| Pyrazolate + Bromobutide | 1 + 5 + 1 | 5 (4.36) | 5 (3.40) | 5 (4.64) | 5 (3.56) | 5 (3.40) | 0 |
| Compound No. 6 + | 0.5 + 5 + 0.5 | 5 (3.80) | 5 (3.40) | 5 (4.64) | 5 (3.56) | 5 (3.40) | 0 |
| Pyrazoxyfen + Bromobutide | 1 + 5 + 1 | 5 (4.36) | 5 (3.40) | 5 (4.64) | 5 (3.56) | 5 (3.40) | 0 |
| Compound No. 6 + | 0.5 + 5 + 0.5 | 5 (3.20) | 5 (3.40) | 5 (4.04) | 5 (3.08) | 5 (3.00) | 0 |
| Bensofenap + Bromobutide | 1 + 5 + 1 | 5 (4.04) | 5 (3.40) | 5 (4.64) | 5 (3.56) | 5 (3.40) | 0 |
| Compound | 0.5 + 5 + 0.5 | 5 | 5 | 5 | 5 | 5 | 0 |

TABLE 5-continued

| Compound No. | Dose (g/a) | Herbicidal effect | | | | | Crop injury |
|---|---|---|---|---|---|---|---|
| | | Echinochloa oryzicola | Broadleaf weeds | Scirpus juncoides | Cyperus serotinus | Sagittaria pygmaea | |
| No. 4 + | | (3.80) | (3.40) | (4.04) | (3.08) | (3.00) | |
| Pyrazolate + | 1 + 5 + 1 | 5 | 5 | 5 | 5 | 5 | 0 |
| Bromobutide | | (4.36) | (3.40) | (4.64) | (3.56) | (3.40) | |
| Compound | 0.5 + 5 + 0.5 | 5 | 5 | 5 | 5 | 5 | 0 |
| No. 4 + | | (3.80) | (3.40) | (4.04) | (3.08) | (3.00) | |
| Pyrazoxyfen + | 1 + 5 + 1 | 5 | 5 | 5 | 5 | 5 | 0 |
| Bromobutide | | (4.36) | (3.40) | (4.64) | (3.56) | (3.40) | |
| Compound | 0.5 + 5 + 0.5 | 5 | 5 | 5 | 5 | 5 | 0 |
| No. 4 + | | (3.20) | (3.40) | (4.04) | (3.08) | (3.00) | |
| Bensofenap + | 1 + 5 + 1 | 5 | 5 | 5 | 5 | 5 | 0 |
| Bromobutide | | (4.04) | (3.40) | (4.64) | (3.56) | (3.40) | |
| Compound | 0.5 + 5 + 0.5 | 5 | 5 | 5 | 5 | 5 | 0 |
| No. 1 + | | (4.20) | (3.00) | (3.80) | (3.08) | (3.00) | |
| Pyrazolate + | 1 + 5 + 1 | 5 | 5 | 5 | 5 | 5 | 0 |
| Bromobutide | | (4.36) | (3.40) | (4.52) | (3.56) | (3.40) | |
| Compound | 0.5 + 5 + 0.5 | 5 | 5 | 5 | 5 | 5 | 0 |
| No. 1 + | | (4.20) | (3.00) | (3.80) | (3.08) | (3.00) | |
| Pyrazoxyfen + | 1 + 5 + 1 | 5 | 5 | 5 | 5 | 5 | 0 |
| Bromobutide | | (4.36) | (3.40) | (4.52) | (3.56) | (3.40) | |
| Compound | 0.5 + 5 + 0.5 | 5 | 5 | 5 | 5 | 5 | 0 |
| No. 1 + | | (3.80) | (3.00) | (3.80) | (3.08) | (3.00) | |
| Bensofenap + | 1 + 5 + 1 | 5 | 5 | 5 | 5 | 5 | 0 |
| Bromobutide | | (4.04) | (3.40) | (4.52) | (3.56) | (3.40) | |
| Compound | 0.5 + 5 + 0.5 | 5 | 5 | 5 | 5 | 5 | 0 |
| No. 10 + | | (3.80) | (3.00) | (3.80) | (3.08) | (3.00) | |
| Pyrazolate + | 1 + 5 + 1 | 5 | 5 | 5 | 5 | 5 | 0 |
| Bromobutide | | (4.36) | (3.40) | (4.52) | (3.56) | (3.40) | |
| Compound | 0.5 + 5 + 0.5 | 5 | 5 | 5 | 5 | 5 | 0 |
| No. 10 + | | (3.80) | (3.00) | (3.80) | (3.08) | (3.00) | |
| Pyrazoxyfen + | 1 + 5 + 1 | 5 | 5 | 5 | 5 | 5 | 0 |
| Bromobutide | | (4.36) | (3.40) | (4.52) | (3.56) | (3.40) | |
| Compound | 0.5 + 5 + 0.5 | 5 | 5 | 5 | 5 | 5 | 0 |
| No. 10 + | | (3.20) | (3.00) | (3.80 | (3.08) | (3.00) | |
| Bensofenap + | 1 + 5 + 1 | 5 | 5 | 5 | 5 | 5 | 0 |
| Bromobutide | | (4.04) | (3.40) | (4.52) | (3.56) | (3.40) | |
| Compound | 1 + 1 | 3 | 5 | 5 | 5 | 3 | 0 |
| No. 6 + | | (3.0) | (2.6) | (3.2) | (2.6) | (2.0) | |
| Clomeprop | 1 + 2 | 4 | 5 | 5 | 5 | 5 | 0 |
| | | (3.0) | (4.2) | (4.4) | (3.2) | (4.0) | |
| Compound | 1 + 2 | 4 | 5 | 5 | 5 | 5 | 0 |
| No. 4 + | | (3.0) | (4.2) | (4.4) | (3.2) | (4.0) | |
| Clomeprop | 2 + 1 | 5 | 5 | 5 | 5 | 4 | 0 |
| | | (5.0) | (3.8) | (3.2) | (4.2) | (2.0) | |
| Compound | 1 + 1 | 4 | 5 | 5 | 5 | 3 | 0 |
| No. 1 + | | (3.0) | (2.6) | (2.6) | (2.6) | (2.0) | |
| Clomeprop | 1 + 2 | 4 | 5 | 5 | 5 | 5 | 0 |
| | | (3.0) | (4.2) | (4.2) | (3.2) | (4.0) | |
| Compound | 1 + 1 | 4 | 5 | 5 | 5 | 3 | 0 |
| No. 10 + | | (3.0) | (2.6) | (2.6) | (2.6) | (2.0) | |
| Clomeprop | 1 + 2 | 4 | 5 | 5 | 5 | 5 | 0 |
| | | (3.0) | (4.2) | (4.2) | (3.2) | (4.0) | |
| Compound | 0.5 + 0.1 | 4 | 5 | 5 | 5 | 5 | 0 |
| No. 6 + | | (2.6) | (5.0) | (4.2) | (4.4) | (4.0) | |
| Bensulfuron | 1 + 0.1 | 5 | 5 | 5 | 5 | 5 | 0 |
| methyl | | (3.4) | (5.0) | (4.4) | (4.4) | (4.0) | |
| Compound | 0.5 + 0.1 | 4 | 5 | 5 | 5 | 5 | 0 |
| No. 6 + | | (3.8) | (5.0) | (5.0) | (5.0) | (4.0) | |
| Pyrazolsulfuron | 1 + 0.1 | 5 | 5 | 5 | 5 | 5 | 0 |
| ethyl | | (4.2) | (5.0) | (5.0) | (5.0) | (4.0) | |
| Compound | 0.5 + 0.1 | 4 | 5 | 5 | 5 | 5 | 0 |
| No. 4 + | | (2.6) | (5.0) | (4.2) | (4.4) | (4.0) | |
| Bensulfuron | 1 + 0.1 | 5 | 5 | 5 | 5 | 5 | 0 |
| methyl | | (3.4) | (5.0) | (4.4) | (4.4) | (4.0) | |
| Compound | 0.5 + 0.1 | 4 | 5 | 5 | 5 | 5 | 0 |
| No. 4 + | | (3.8) | (5.0) | (5.0) | (5.0) | (4.0) | |
| Pyrazosulfuro | 1 + 0.1 | 5 | 5 | 5 | 5 | 5 | 0 |
| ethyl | | (4.2) | (5.0) | (5.0) | (5.0) | (4.0) | |
| Compound | 0.5 + 0.1 | 4 | 5 | 5 | 5 | 5 | 0 |
| No. 1 + | | (3.4) | (5.0) | (4.0) | (4.4) | (4.0) | |
| Bensulfuron | 1 + 0.1 | 5 | 5 | 5 | 5 | 5 | 0 |
| methyl | | (3.4) | (5.0) | (4.2) | (4.4) | (4.0) | |
| Compound | 0.5 + 0.1 | 5 | 5 | 5 | 5 | 5 | 0 |
| No. 1 + | | (4.2) | (5.0) | (5.0) | (5.0) | (4.0) | |
| Pyrazosulfuro | 1 + 0.1 | 5 | 5 | 5 | 5 | 5 | 0 |
| ethyl | | (4.2) | (5.0) | (5.0) | (5.0) | (4.0) | |
| Compound | 0.5 + 0.1 | 4 | 5 | 5 | 5 | 5 | 0 |
| No. 10 + | | (2.6) | (5.0) | (4.0) | (4.4) | (4.0) | |
| Bensulfuron | 1 + 0.1 | 5 | 5 | 5 | 5 | 5 | 0 |
| methyl | | (3.4) | (5.0) | (4.2) | (4.4) | (4.0) | |

TABLE 5-continued

| Compound No. | Dose (g/a) | Herbicidal effect | | | | | Crop injury |
|---|---|---|---|---|---|---|---|
| | | Echinochloa oryzicola | Broadleaf weeds | Scirpus juncoides | Cyperus serotinus | Sagittaria pygmaea | |
| Compound No. 10 + | 0.5 + 0.1 | 4 (3.8) | 5 (5.0) | 5 (5.0) | 5 (5.0) | 5 (4.0) | 0 |
| Pyrazosulfuro ethyl | 1 + 0.1 | 5 (4.2) | 5 (5.0) | 5 (5.0) | 5 (5.0) | 5 (4.0) | 0 |
| Compound No. 6 + | 0.5 + 0.1 | 4 (2.6) | 5 (5.0) | 5 (4.2) | 5 (4.4) | 5 (4.0) | 0 |
| CG-148 | 1 + 0.1 | 5 (3.4) | 5 (5.0) | 5 (4.4) | 5 (4.4) | 5 (4.0) | 0 |
| Compound No. 4 + | 0.5 + 0.1 | 4 (2.6) | 5 (5.0) | 5 (4.2) | 5 (4.4) | 5 (4.0) | 0 |
| CG-148 | 1 + 0.1 | 5 (3.4) | 5 (5.0) | 5 (4.4) | 5 (4.4) | 5 (4.0) | 0 |
| Compound No. 1 + | 0.5 + 0.1 | 4 (3.4) | 5 (5.0) | 5 (4.0) | 5 (4.4) | 5 (4.0) | 0 |
| CG-148 | 1 + 0.1 | 5 (3.4) | 5 (5.0) | 5 (4.2) | 5 (4.4) | 5 (4.0) | 0 |
| Compound No. 10 + | 0.5 + 0.1 | 4 (2.6) | 5 (5.0) | 5 (4.0) | 5 (4.4) | 5 (4.0) | 0 |
| CG-148 | 1 + 0.1 | 5 (3.4) | 5 (5.0) | 5 (4.2) | 5 (4.4) | 5 (4.0) | 0 |

The data in Table 5 shows that the measured "percent control" values of most of the herbicide combinations tested were greater than the corresponding "expected" responses. It is therefore clear that combinations of compounds of the general formula I with known herbicides exhibit synergistic effects.

The following are several examples of formulations of the herbicide of the present invention.

| Formulation Example 1 (Granule) | |
|---|---|
| Compound No. 2 | 1.5 (parts by weight) |
| Sodium lignin sulfonate | 2.0 |
| Bentonite | 30.0 |
| Talc | 66.5 |

These components were intimately mixed to obtain a homogeneous composition, which was granulated to form granules.

| Formulatin Example 2 (Wettable powder) | |
|---|---|
| Compound No. 20 | 50 (parts by weight) |
| Sodium alkylsulfate | 3.5 |
| Polyoxyethylene alkylphenyl ether | 2.5 |
| Clay | 45 |

These components were intimately mixed to obtain a homogeneous composition, which was finely ground to form a wettable powder.

| Formulation Example 3 (Emulsifiable concentrate) | |
|---|---|
| Compound No. 6 | 20 (parts by weight) |
| Alkylbenzenesulfonate salt | 3 |
| Polyoxyethylene alkyl-arylether | 10 |
| Xylol | 67 |

These components were intimately mixed to obtain a homogeneous emulsifiable concentrate.

| Formulation Example 4 (Granule) | |
|---|---|
| Compound No. 6 | 1 (part by weight) |
| Pyrazolate | 4 |

| Formulation Example 4 (Granule) -continued | |
|---|---|
| Sodium lignin sulfonate | 2 |
| Bentonite | 30 |
| Talc | 63 |

These components were intimately mixed to obtain a homogeneous composition, which was granulated to form granules.

| Formulation Example 5 (Wettable powder) | |
|---|---|
| Compound No. 1 | 30 (parts by weight) |
| Bensulfuron methyl | 6 |
| Sodium alkylsulfate | 2.5 |
| Polyoxyethylene alkylphenyl ether | 2.5 |
| Clay | 59 |

These components were intimately mixed to obtain a homogeneous composition, which was finely ground to form a wettable powder.

| Formulation Example 6 (Emulsifiable concentrate) | |
|---|---|
| Compound No. 10 | 20 (parts by weight) |
| CG-148 | 4 |
| Alkylbenzenesulfonate salt | 3 |
| Polyoxyethylene alkylaryl ether | 10 |
| Xylol | 63 |

These components were intimately mixed to obtain a homogeneous emulsifiable concentrate.

What is claimed is:

1. A triazole compound of the formula:

$$A-S(O)_n-\underset{N}{\underset{\|}{C}}\diagup \overset{N-N}{\underset{N}{\diagdown}} -CON\diagup \overset{R_1}{\diagdown} R_2$$

where
R₁ and R₂ which may be the same or different each represents ethyl or n-propyl;

A represents a group represented by one of the following formulas:

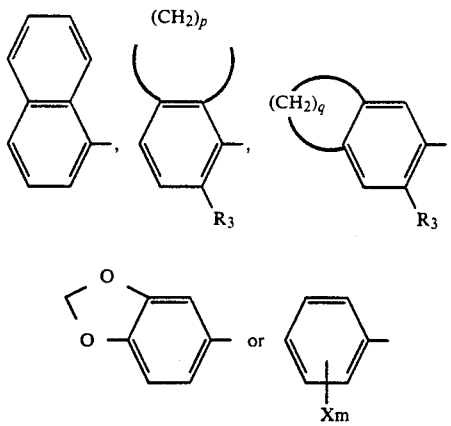

(where X is a hydrogen atom or an optionally hydroxyl substituted lower alkyl, cycloalkyl, alkoxy, alkoxycarbonyl, alkylcarbonyl, phenoxy, benzyl or α-hydroxybenzyl group, a halogen, a nitro group, an amino group or a trifluoromethyl group; $R_3$ is a hydrogen atom or lower alkoxy; m is 0, 1, 2, 3 or 4; n is 0 or 2; and p and q are each 2, 3, 4 or 5).

2. A herbicidal composition containing from 0.05 to 95% by weight of an effective ingredient a triazole compound of the formula:

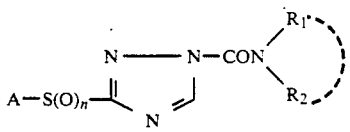

(where A, n, $R_1$ and $R_2$ have the same meanings as defined in claim 1).

3. The herbicidal composition according to claim 2 wherein the effective ingredient is present in amounts ranging from 1 to 70% by weight.

4. A compound according to claim 1 which is 1-(Diethylcarbamoyl)-3-(2-nitrophenylthio)-1,2,4-Triazole.

5. A compound according to claim 1 which is 1-(Diethylcarbamoyl)-3-(2-Chloro-4-Trifluoromethyl-Phenylsulfonyl)-1,2,4-Triazole.

6. A compound according to claim 1 which is 1-(Diethylcarbamoyl)-3-(2,6-Dimethylphenylsulfonyl)-1,2,4-Triazole.

7. A compound according to claim 1 which is 1-(Diethylcarbamoyl)-3-(2,4,5-Trimethyl-6-Methoxyphenylsulfonyl)-1,2,4-Triazole.

8. A compound according to claim 1 which is 1-(Diethylcarbamoyl)-3-(2-Methyl-6-Ethylphenylsulfonyl)-1,2,4-Triazole.

9. A compound according to claim 1 wherein $R_1$ and $R_2$ are ethyl, n is 2, and $X_m$ is 2-Cl.

10. A compound according to claim 1 which is 1-(diethylcarbamoyl)-3-(2,4,6-trimethylphenyl sulfonyl)-1,2,4-triazole.

* * * * *

UNITED STATES PATENT AND TRADEMARK OFFICE
CERTIFICATE OF CORRECTION

PATENT NO.  : 5,147,445
DATED       : Sep. 15, 1992
INVENTOR(S) : TAKEUCHI et al.

It is certified that error appears in the above-identified patent and that said Letters Patent is hereby corrected as shown below:

Title page,
Column 1, Item [63], delete "Jun. 6, 1989, and insert therefore --Mar. 6, 1989--; and Title page,
Column 1, Item [30], delete "Jul. 5, 1988 [JP] Japan..........63-16712" and insert therefore --July 5, 1988 [JP] Japan..........63-167128--.

Signed and Sealed this

Thirtieth Day of November, 1993

Attest:

BRUCE LEHMAN

Attesting Officer

Commissioner of Patents and Trademarks